US008153805B2

(12) United States Patent
Aebi et al.

(10) Patent No.: US 8,153,805 B2
(45) Date of Patent: Apr. 10, 2012

(54) BIARYL DERIVATIVES

(75) Inventors: Johannes Aebi, Binningen (CH); Alfred Binggeli, Binningen (CH); Luke Green, Basel (CH); Guido Hartmann, Loerrach (DE); Hans P Maerki, Basel (CH); Patrizio Mattei, Riehen (CH); Fabienne Ricklin, Hombourg (FR); Olivier Roche, Folgensbourg (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 690 days.

(21) Appl. No.: 12/239,055

(22) Filed: Sep. 26, 2008

(65) Prior Publication Data

US 2009/0048238 A1    Feb. 19, 2009

(30) Foreign Application Priority Data

Oct. 1, 2007    (EP) ..................................... 07117656

(51) Int. Cl.
*C07D 211/68* (2006.01)
*A61K 31/445* (2006.01)

(52) U.S. Cl. ....................................... 546/194; 514/318

(58) Field of Classification Search ................... 546/194; 514/318
See application file for complete search history.

(56) References Cited

U.S. PATENT DOCUMENTS

| 6,136,826 A | 10/2000 | Fujioka et al. |
| 2004/0067961 A1 | 4/2004 | Baroudy et al. |
| 2005/0277668 A1 | 12/2005 | Zhou et al. |

FOREIGN PATENT DOCUMENTS

| DE | 2538950 | 3/1977 |
| EP | 1 632 479 | 3/2006 |
| WO | WO 01/77101 | 10/2001 |
| WO | WO 02/074741 | 9/2002 |
| WO | WO 03/020716 | 3/2003 |
| WO | WO 2004/031172 | 4/2004 |
| WO | WO 2004/043925 | 5/2004 |
| WO | WO 2005/097740 | 10/2005 |
| WO | WO 2006/021759 | 3/2006 |
| WO | WO 2006/114401 | 11/2006 |
| WO | WO 2007/116313 | 10/2007 |
| WO | WO 2008/060621 | 5/2008 |

OTHER PUBLICATIONS

Kuno et al. (Chemical & Pharmaceutical Bulletin (1992), 40(9), 2423-31).*
Wermuth (The Practice of Medicinal Chemsitry, 2d ed. (2003), 768 pages), chapters 13 and 19 provided.*
Kubinyi (3D QSAR in Drug Design: Ligand-Protein Interactions and Molecular Similarity, vol. 2-3, Springer, 1998, 800 pages), TOC and pp. 243-44 provided.*
Wermuth (The Practice of Medicinal Chemsitry, 2d ed. (2003), 768 pages), Chapters 9-10 provided.*
Yang et al. (Bioorg. Med. Chem. Lett. 16 (2006) 3735-3739).*
Bundgaard (Design and application of prodrugs, In a Textbook of Drug Design and Development, (1991), p. 113-191).*
Thoma et al., J. Medicinal Chemistry, 47(8), pp. 1939-1955 (2004) XP002509541.
Database Caplus accession No. 2008 :1079950 XP002509542.
Database Caplus accession No. 1978 :443156 XP002527302.
Fuson et al., J. American Chem. Soc., 63, pp. 1679-1682 (1941).
Reim et al., Tetrahedron Lett., 47, pp. 6903-6905 (2006).
McCombie et al., Bioorg. Medicinal Chem. Lett., 13, pp. 567-571 (2003).
Kato et al., Chem. Pharma. Bull., 28(7), pp. 2244-2247 (1980).
Jung et al., Tetrahedron, 58, pp. 3639-3646 (2002).
Marusawa et al., Bioorg. Medicinal Chem., 10, pp. 1399-1415 (2002).
Chan et al., J. Medicinal Chem., 44, pp. 1866-1882 (2001).
Lee et al., Bioorg. Medicinal Chem. Lett., 13, pp. 1879-1882 (2003).
Chilean Notice of Opposition in patent application 24529CL.

* cited by examiner

*Primary Examiner* — Robert Havlin
(74) *Attorney, Agent, or Firm* — George W. Johnston; Patricia S. Rocha-Tramaloni; Gene J. Yao

(57) ABSTRACT

The invention is concerned with novel biaryl derivatives of formula (I), wherein m, $R^1$, $R^2$, $R^3$, $X^1$, $X^2$ and $X^3$ are as defined in the description and in the claims, as well as physiologically acceptable salts thereof. These compounds are antagonists of CCR-2 receptor, CCR-5 receptor and/or CCR-3 receptor and can be used as medicaments.

13 Claims, No Drawings

BIARYL DERIVATIVES

PRIORITY TO RELATED APPLICATION(S)

This application claims the benefit of European Patent Application No. 07117556.4, filed Oct. 1, 2007, which is hereby incorporated by reference in its entirety.

FIELD OF THE INVENTION

The present invention is directed to, for example, novel biaryl derivatives, their manufacture and their use as medicaments. In particular, the present invention provides the novel compounds of formula (I) which are CCR2 receptor antagonists, with some antagonist activity also at CCR-3 and CCR-5, and pharmaceutically acceptable compositions thereof.

BACKGROUND OF THE INVENTION

Chemokines are a family of small, secreted proinflammatory cytokines functioning as chemoattractants for leukocytes. They promote trafficking of leukocytes from vascular beds into surrounding tissues in response to inflammatory signals. Chemotaxis starts upon chemokine binding to receptors (GPCRs) by initiating signaling pathways involving increased Ca-flux, inhibition of cAMP production, rearrangements of the cytoskeleton, activation of integrins and of cell motility processes and an increase in the expression of adhesion proteins.

Proinflammatory chemokines are considered to be involved in the development of atherosclerosis and other important diseases with inflammatory components like rheumatoid arthritis, asthma, multiple sclerosis, transplant rejection and ischemia reperfusion injury with specific prominent effects in nephropathy and peripheral vascular diseases. Monocyte Chemotactic Protein 1 is considered to be the major stimulated chemokine mediating inflammatory processes in these diseases through the CCR2 receptor on monocytes and on some T lymphocytes. In addition MCP-1/CCR2 are in discussion to be related to the progression of the metabolic syndrome to more severe stages of obese and diabetic diseases.

CCR2 has also been linked to HIV infection, and consequently the course of autoimmune diseases, through its heterodimerization with CCR5 which has a role as coreceptor for viral entry into host cells.

Thus, CCR2 can be a target of a new medicine for treatment of peripheral vascular diseases, and more specifically for treatment of patients with critical limb ischemia. Furthermore, study results and experiences from the development of a new CCR2 medicine for this indication may facilitate a follow-up development for treatment of atherosclerosis. There is a large body of information from animal models of MCP-1 and CCR2 ko mice in wt or apoE−/− or LDL-R−/− backgrounds showing that the MCP-1/CCR2 pathway is essential for monocyte/macrophage recruitment, and also for intimal hyperplasia and the formation and stability of atherosclerotic lesions. In addition, numerous reports describe involvement of the MCP-1/CCR2 pathway in man post injury and in various inflammatory processes, including such in vascular beds.

SUMMARY OF THE INVENTION

The invention is concerned with novel biaryl derivatives of formula (I),

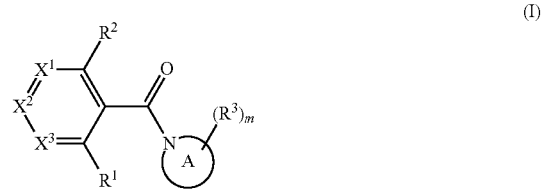

, wherein $R^1$ is halogen, $C_{1-6}$ alkyl, $C_{1-6}$ alkoxy, halo $C_{1-6}$ alkyl, heteroalkyl, $C_{1-6}$ alkylsulfanyl, $C_{1-6}$ alkylsulfinyl, $C_{1-6}$ alkylsulfonyl, $C_{3-7}$ cycloalkyl or $C_{3-7}$ cycloalkyl $C_{1-6}$ alkyl;

$R^2$ is hydrogen, $C_{1-6}$ alkyl, halo $C_{1-6}$ alkyl, trimethylsilanyl $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, trimethylsilanyl $C_{2-6}$ alkynyl, hydroxy, $C_{1-6}$ alkoxy, halo $C_{1-6}$ alkoxy, heteroalkoxy, optionally substituted $C_{3-7}$ cycloalkyl, optionally substituted $C_{3-7}$ cycloalkyl $C_{1-6}$ alkyl, halogen, cyano, optionally substituted phenyl, optionally substituted heteroaryl, optionally substituted heterocyclyl or optionally substituted phenylmethoxy $C_{1-6}$ alkoxy, provided that optionally substituted phenyl does not have nitro as a substituent;

$R^3$ is, when attached to a ring carbon atom, independently hydrogen, $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, halogen, cyano, optionally substituted phenyl, optionally substituted $C_{3-7}$ cycloalkyl, optionally substituted $C_{3-7}$ cycloalkyl $C_{1-6}$ alkyl, optionally substituted heteroaryl, optionally substituted heterocyclyl, optionally substituted phenyl-$C_{1-6}$ alkyl, optionally substituted heteroaryl-$C_{1-6}$ alkyl, optionally substituted heterocyclyl-$C_{1-6}$ alkyl, nitro, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl or $C_{1-6}$ alkylsulfonyl or amino optionally substituted by one or two substituents independently selected from the group consisting of $C_{1-6}$ alkyl, heteroalkyl, optionally substituted $C_{3-7}$ cycloalkyl and optionally substituted heterocyclyl; or when attached to a ring nitrogen atom, independently hydrogen, $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, optionally substituted $C_{3-7}$ cycloalkyl or optionally substituted $C_{3-7}$ cycloalkyl $C_{1-6}$ alkyl, optionally substituted heterocyclyl, or optionally substituted heterocyclyl $C_{1-6}$ alkyl;

m is 0, 1, 2, 3 or 4;

is heterocyclyl, which is a non-aromatic mono-cyclic radical of four to eight ring atoms, in which one or two ring atoms are nitrogen atoms, the remaining ring atoms being carbon atoms;

one of $X^1$, $X^2$ and $X^3$ is C—$R^4$, the others are independently N or C—$R^5$;

$R^4$ is phenyl or heteroaryl, which is an aromatic mono-cyclic radical of six ring atoms, in which one or two ring atoms are nitrogen atoms, the remaining ring atoms being carbon atoms, and said phenyl and said heteroaryl are substituted by one, two or three substituents independently selected from the group consisting of $C_{1-8}$ alkyl, halo $C_{1-6}$ alkyl, $C_{1-6}$ alkoxy, halo $C_{1-6}$ alkyoxy, halogen and cyano;

$R^5$ is hydrogen, $C_{1-6}$ alkyl, $C_{1-6}$ alkoxy, halo $C_{1-6}$ alkyl or halogen;

provided that

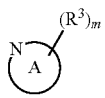

contains at least one nitrogen atom, which is not directly bonded to a carbonyl group or a heteoratom; and

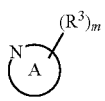

does not contain a nitrogen atom, which is directly bonded to a heteroatom; and provided that

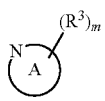

is not 2-(optionally substituted pyrrolidin-1-yl $C_{1-6}$ alkyl)-pyrrolidine-1-yl;

or prodrugs or pharmaceutically acceptable salts thereof.

Further, the invention is concerned with a process for the manufacture of the above compounds, pharmaceutical preparations which contain such compounds, the use of these compounds for the production of pharmaceutical preparations.

DETAILED DESCRIPTION OF THE INVENTION

A. Definitions

Unless otherwise indicated, the following definitions are set forth to illustrate and define the meaning and scope of the various terms used to describe the invention herein.

The term "heteroatom" means a nitrogen atom, an oxygen atom or a sulphur atom.

The term "halogen" or "halo" means fluorine, chlorine, bromine and iodine, with chlorine and fluorine being preferred.

The term "$C_{1-6}$ alkyl", alone or in combination with other groups, means a branched or straight-chain monovalent alkyl radical, having one to six carbon atoms. This term is further exemplified by such radicals as methyl, ethyl, n-propyl, iso-propyl, n-butyl, s-butyl, t-butyl. $C_{1-4}$ alkyl or $C_{1-3}$ alkyl is more preferred.

The term "hydroxy $C_{1-6}$ alkyl" means $C_{1-6}$ alkyl substituted by one or more, preferably one hydroxy group(s).

The term "halo $C_{1-6}$ alkyl" means $C_{1-6}$ alkyl substituted by one or more same or different halogen atoms.

The term "$C_{1-6}$ alkylene", alone or in combination with other groups, means a branched or straight-chain saturated divalent hydrocarbon radical of one to six carbon atoms, such as methylene, ethylene, tetramethylethylene.

The term "$C_{3-7}$ cycloalkyl", alone or in combination with other groups, means a saturated monovalent mono-cyclic hydrocarbon radical of three to seven ring carbons, e.g., cyclopropyl, cyclobutyl, cyclohexyl.

The term "$C_{1-6}$ alkoxy", alone or in combination with other groups, means the group R'—O—, wherein R' is a $C_{1-6}$ alkyl.

The term "halo $C_{1-6}$ alkoxy", alone or in combination with other groups, means $C_{1-6}$ alkoxy substituted by one or more, preferably one to three halogens.

The term "$C_{2-6}$ alkenyl", alone or in combination with other groups, means a straight-chain or branched hydrocarbon residue comprising a carbon-carbon double bond, having two to six carbon atoms. This term is further exemplified by such radicals as ethenyl, 2-propenyl.

The term "hydroxy $C_{3-6}$ alkenyl" or "$C_{1-6}$ alkoxy $C_{3-6}$ alkenyl" means $C_{3-6}$ alkenyl substituted by one or more, preferably one or two hydroxy groups or $C_{1-6}$ alkoxy groups, respectively.

The term "$C_{2-6}$-alkynyl", alone or in combination with other groups, means a straight-chain or branched hydrocarbon residue comprising a carbon-carbon triple bond, having two to six carbon atoms. This term is further exemplified by such radicals as ethynyl, 2-propynyl.

The term "hydroxy $C_{3-6}$ alkynyl" or "$C_{1-6}$ alkoxy $C_{3-6}$ alkenyl" means $C_{3-6}$ alkynyl substituted by one or more, preferably one or two hydroxy groups or $C_{1-6}$ alkoxy groups, respectively.

The term "acyl" means R—C(O)—, in which R is $C_{1-6}$ alkyl, halo $C_{1-6}$ alkyl, $C_{3-7}$ cycloalkyl or $C_{3-7}$ cycloalkyl $C_{1-6}$ alkyl.

The term "heteroalkyl" means $C_{1-6}$ alkyl substituted by one or more substituents selected independently from the group consisting of nitro, hydroxy, cyano, $C_{1-6}$ alkoxy, formyl, acyl, carboxyl, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heteroalkoxy" means $C_{1-6}$ alkoxy substituted by one or more substituents selected independently from the group consisting of nitro, hydroxy, cyano, $C_{1-6}$ alkoxy, formyl, acyl, carboxyl, $C_{1-6}$ alkylthio, $C_{1-6}$ alkyl sulfinyl, $C_{1-6}$ alkyl sulfonyl, carbamoyl, amino and mono- or di-$C_{1-6}$ alkyl substituted amino.

The term "heterocyclyl" means non-aromatic mono-cyclic radicals of four to seven ring atoms, in which one to three ring atoms are heteroatoms independently selected from N, O and $S(O)_n$ (where n is an integer from 0 to 2), the remaining ring atoms being C.

The term "heteroaryl" means an aromatic mono-cyclic radical of 5 or 6 ring atoms, having one to three ring heteroatoms independently selected from N, O, and S, the remaining ring atoms being C.

The term "optionally substituted $C_{3-7}$ cycloalkyl" means $C_{3-7}$ cycloalkyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term "optionally substituted phenyl" means a phenyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term "optionally substituted heterocyclyl" means a heterocyclyl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term "optionally substituted heteroaryl" means a heteroaryl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term "optionally substituted pyrrolidin-1-yl" means a pyrrolidin-1-yl optionally substituted by one to three substituents independently selected from the group consisting of $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, $C_{3-7}$ cycloalkyl, $C_{3-7}$ cycloalkyl $C_{1-6}$ alkyl, halogen, cyano, nitro, amino, mono- or di-$C_{1-6}$ alkyl substituted amino, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl, $C_{1-6}$ alkylsulfonyl and acylamino.

The term, "$C_{1-6}$ alkylsulfonyl", "$C_{1-6}$ alkylsulfinyl" and "$C_{1-6}$ alkylthio", alone or combination with other groups, means $C_{1-6}$ alkyl-$SO_2$—, $C_{1-6}$ alkyl-SO— and $C_{1-6}$ alkyl-S—, respectively.

Preferred radicals for the chemical groups whose definitions are given above are those specifically exemplified in Examples.

Compounds of formula (I) can form pharmaceutically acceptable acid addition salts. Examples of such pharmaceutically acceptable salts are salts of compounds of formula (I) with physiologically compatible mineral acids, such as hydrochloric acid, hydrobromic acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts.

"Optional" or "optionally" means that the subsequently described event or circumstance may but need not occur, and that the description includes instances where the event or circumstance occurs and instances in which it does not. For example, "aryl group optionally substituted with an alkyl group" means that the alkyl may but need not be present, and the description includes situations where the aryl group is substituted with an alkyl group and situations where the aryl group is not substituted with the alkyl group.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Compounds that have the same molecular formula but differ in the nature or sequence of bonding of their atoms or the arrangement of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, if a carbon atom is bonded to four different groups, a pair of enantiomers is possible. An enantiomer can be characterized by the absolute configuration of its asymmetric center and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of formula (I) can possess one or more asymmetric centers. Unless indicated otherwise, the description or naming of a particular compound in the specification and claims is intended to include both individual enantiomers and mixtures, racemic or otherwise, thereof, as well as individual epimers and mixture thereof. The methods for the determination of stereochemistry and the separation of stereoisomers are well-known in the art (see discussion in Chapter 4 of "Advanced Organic Chemistry", 4th edition J. March, John Wiley and Sons, New York, 1992). All references cited herein are incorporated by reference in their entirety.

B. Detailed Description of the Invention

The compounds of formula (I) are CCR2 receptor (Chemokine Receptor 2/Monocyte Chemotactic Protein 1 Receptor) antagonists and also CCR-5 receptor (Chemokine Receptor 5) and/or CCR-3 receptor (Chemokine Receptor 3) antagonists.

The invention is concerned with novel biaryl derivatives of formula (I),

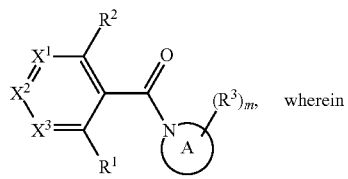

wherein

R¹ is halogen, $C_{1-6}$ alkyl, $C_{1-6}$ alkoxy, halo $C_{1-6}$ alkyl, heteroalkyl, $C_{1-6}$ alkylsulfanyl, $C_{1-6}$ alkylsulfinyl, $C_{1-6}$ alkylsulfonyl, $C_{3-7}$ cycloalkyl or $C_{3-7}$ cycloalkyl $C_{1-6}$ alkyl;

R² is hydrogen, $C_{1-6}$ alkyl, halo $C_{1-6}$ alkyl, trimethylsilanyl $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, trimethylsilanyl $C_{2-6}$ alkynyl, hydroxy, $C_{1-6}$ alkoxy, halo $C_{1-6}$ alkoxy, heteroalkoxy, optionally substituted $C_{3-7}$ cycloalkyl, optionally substituted $C_{3-7}$ cycloalkyl $C_{1-6}$ alkyl, halogen, cyano, optionally substituted phenyl, optionally substituted heteroaryl, optionally substituted heterocyclyl or optionally substituted phenylmethoxy $C_{1-6}$ alkoxy,
provided that optionally substituted phenyl does not have nitro as a substituent;

R³ is, when attached to a ring carbon atom, independently hydrogen, $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, halogen, cyano, optionally substituted phenyl, optionally substituted $C_{3-7}$ cycloalkyl, optionally substituted $C_{3-7}$ cycloalkyl $C_{1-6}$ alkyl, optionally substituted heteroaryl, optionally substituted heterocyclyl, optionally substituted phenyl-$C_{1-6}$ alkyl, optionally substituted heteroaryl-$C_{1-6}$ alkyl, optionally substituted heterocyclyl-$C_{1-6}$ alkyl, nitro, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl or $C_{1-6}$ alkylsulfonyl or amino optionally substituted by one or two substituents independently selected from the group consisting of $C_{1-6}$ alkyl, heteroalkyl, optionally substituted $C_{3-7}$ cycloalkyl and optionally substituted heterocyclyl; or
 when attached to a ring nitrogen atom, independently hydrogen, $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, optionally substituted $C_{3-7}$ cycloalkyl or optionally substituted $C_{3-7}$ cycloalkyl $C_{1-6}$ alkyl, optionally substituted heterocyclyl, or optionally substituted heterocyclyl $C_{1-6}$ alkyl;

m is 0, 1, 2, 3 or 4;

is heterocyclyl, which is a non-aromatic mono-cyclic radical of four to eight ring atoms, in which one or two ring atoms are nitrogen atoms, the remaining ring atoms being carbon atoms;

one of X¹, X² and X³ is C—R⁴, the others are independently N or C—R⁵;

R⁴ is phenyl or heteroaryl, which is an aromatic mono-cyclic radical of six ring atoms, in which one or two ring atoms are nitrogen atoms, the remaining ring atoms being carbon atoms, and said phenyl and said heteroaryl are substituted by one, two or three substituents independently selected from the group consisting of $C_{1-8}$ alkyl, halo $C_{1-6}$ alkyl, $C_{1-6}$ alkoxy, halo $C_{1-6}$ alkyoxy, halogen and cyano;

R⁵ is hydrogen, $C_{1-6}$ alkyl, $C_{1-6}$ alkoxy, halo $C_{1-6}$ alkyl or halogen;

provided that

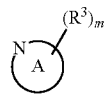

contains at least one nitrogen atom, which is not directly bonded to a carbonyl group or a heteroatom; and

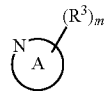

does not contain a nitrogen atom, which is directly bonded to a heteroatom; and provided that

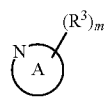

is not 2-(optionally substituted pyrrolidin-1-yl $C_{1-6}$ alkyl)-pyrrolidine-1-yl;

or prodrugs or pharmaceutically acceptable salts thereof.

Further, the invention is concerned with a process for the manufacture of the above compounds, pharmaceutical preparations which contain such compounds, the use of these compounds for the production of pharmaceutical preparations.

While the broadest definition of this invention is described before, certain compounds of formula (I) are preferred.

i) In the compounds of formula (I),

is preferably pyrrolidin-1-yl, piperidin-1-yl or [1,4]diazepan-1-yl, more preferably piperidin-1-yl.

ii) In the compounds of formula (I), m is preferably 1.

iii) In the compounds of formula (I), R³ is preferably optionally substituted heterocyclyl or heteroalkyl, more preferably hydroxy $C_{1-6}$ alkyl, optionally substituted pyrrolidin-1-yl or optionally substituted piperidin-1-yl, further more preferably R³ is piperidin-1-yl or pyrrolidin-1-yl, said piperidin-1-yl and pyrrolidin-1-yl being optionally substituted by hydroxyl $C_{1-6}$ alkyl or hydroxy. R³ is especially pyrrolidin-1-yl, 2-hydroxymethyl-pyrrolidin-1-yl or 4-hydroxy-piperidin-1-yl.

iv) In the compounds of formula (I),

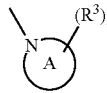

is preferably 4-pyrrolidin-1-yl-piperidin-1-yl, 4-(2-hydroxymethyl-pyrrolidin-1-yl)-piperidin-1-yl or 4-hydroxy-[1,4']bipiperidinyl-1'-yl.
v) In the compounds of formula (I), $R^1$ is preferably halogen or $C_{1-6}$ alkyl and $R^2$ is preferably hydrogen, hydroxy, halogen, $C_{1-6}$ alkyl, optionally substituted heteroaryl, heteroalkoxy or cyclopropyl. $R^1$ is more preferably fluorine or methyl and $R^2$ is more preferably hydrogen, hydroxy, fluorine, methyl, pyrimidinyl, pyridinyl, hydroxyethoxy or cyclopropyl.
vi) In the compounds of formula (I), $R^1$ is preferably $C_{1-6}$ alkyl and $R^2$ is hydrogen, $C_{1-6}$ alkyl or cyclopropyl, more preferably $R^1$ is methyl and $R^2$ is methyl or cyclopropyl.
vii) In the compounds of formula (I), preferably $X^1$ is C—$R^4$ and $X^2$ and $X^3$ are C—$R^5$, in which $R^4$ is preferably phenyl substituted by halo $C_{1-6}$ alkyl or halo $C_{1-6}$ alkyoxy and $R^5$ is preferably hydrogen.
viii) In the compounds of formula (I), preferably $X^2$ is C—$R^4$ and both $X^1$ and $X^3$ are N or C—$R^5$, in which $R^4$ is preferably phenyl or pyridyl, said phenyl and pyridyl being substituted by halo $C_{1-6}$ alkyl or halo $C_{1-6}$ alkyoxy and $R^5$ is preferably hydrogen.
ix) A preferred compound of the invention is a compound of formula (I), which is
(3,5-Dimethyl-3'-trifluoromethoxy-biphenyl-4-yl)-(4-pyrrolidin-1-yl-piperidin-1-yl)-methanone,
(3,5-Dimethyl-3'-trifluoromethyl-biphenyl-4-yl)-(4-pyrrolidin-1-yl-piperidin-1-yl)-methanone,
(3,5-Dimethyl-3'-trifluoromethyl-biphenyl-4-yl)-[4-((S)-2-hydroxymethyl-pyrrolidin-1-yl)-piperidin-1-yl]-methanone,
[2,6-Dimethyl-4-(5-trifluoromethyl-pyridin-3-yl)-phenyl]-[4-((S)-2-hydroxymethyl-pyrrolidin-1-yl)-piperidin-1-yl]-methanone,
[4-Cyclopropyl-6-methyl-2-(3-trifluoromethyl-phenyl)-pyrimidin-5-yl]-(4-pyrrolidin-1-yl-piperidin-1-yl)-methanone,
(3,5-Dimethyl-3'-trifluoromethyl-biphenyl-4-yl)-(4-hydroxy-[1,4']bipiperidinyl-1'-yl)-methanone,
[2,4-Dimethyl-6-(3-trifluoromethyl-phenyl)-pyridin-3-yl]-(4-pyrrolidin-1-yl-piperidin-1-yl)-methanone,
(3,5-Difluoro-3'-trifluoromethyl-biphenyl-4-yl)-(4-pyrrolidin-1-yl-piperidin-1-yl)-methanone,
(5-Methyl-3-pyrimidin-5-yl-3'-trifluoromethyl-biphenyl-4-yl)-(4-pyrrolidin-1-yl-piperidin-1-yl)-methanone,
(5-Methyl-3-pyridin-3-yl-3'-trifluoromethyl-biphenyl-4-yl)-(4-pyrrolidin-1-yl-piperidin-1-yl)-methanone,
[2-Hydroxy-4-methyl-6-(3-trifluoromethyl-phenyl)-pyridin-3-yl]-(4-pyrrolidin-1-yl-piperidin-1-yl)-methanone; 4-Methyl-3-(4-pyrrolidin-1-yl-piperidine-1-carbonyl)-6-(3-trifluoromethyl-phenyl)-1H-pyridin-2-one, or
[2-(2-Hydroxy-ethoxy)-4-methyl-6-(3-trifluoromethyl-phenyl)-pyridin-3-yl]-(4-pyrrolidin-1-yl-piperidin-1-yl)-methanone.

General Synthetic Procedures

The compounds of formula (I) can be manufactured by methods known in the art, by the methods given below, by the methods given in the examples or by analogous methods. Appropriate reaction conditions for the individual reaction steps are known to a person skilled in the art. Starting materials are either commercially available or are known or can be prepared by methods given below or by methods described in the examples, or by methods known in the art.

The syntheses of the compounds of general formula (I) are described in Scheme 1 to Scheme 9.

Scheme 1

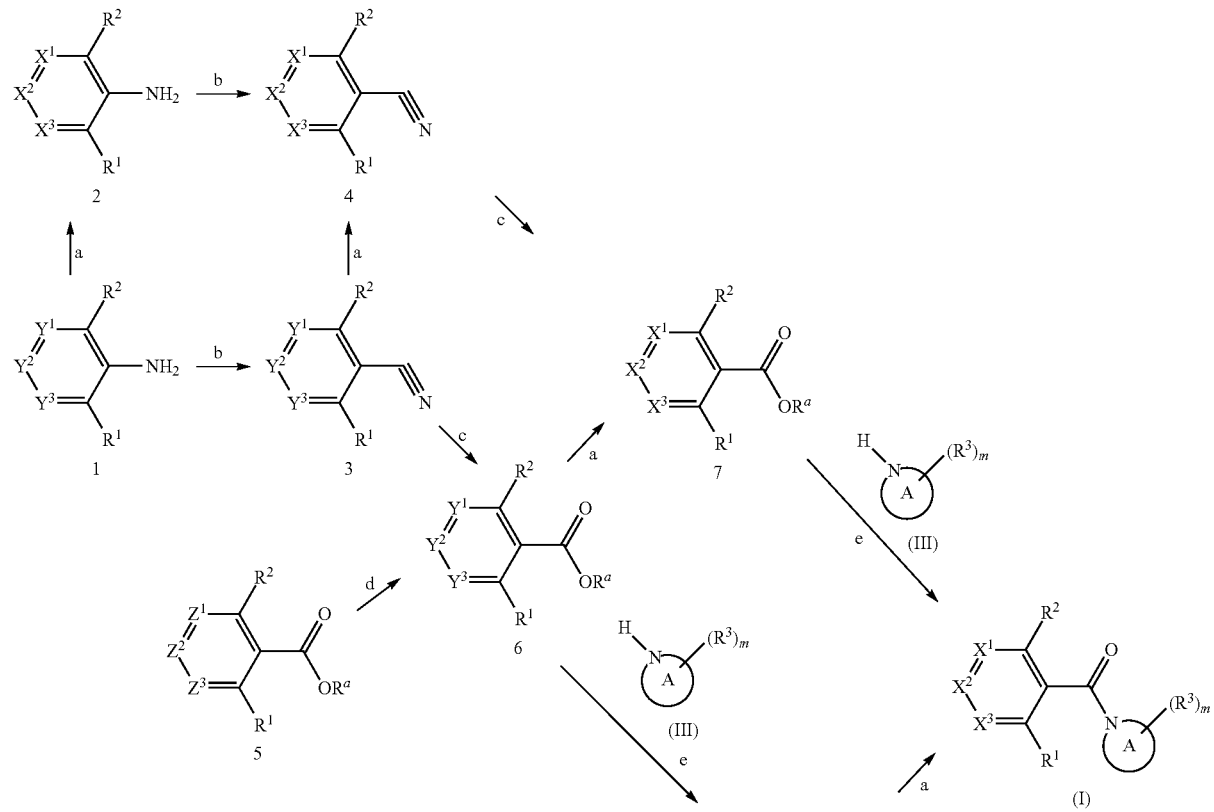

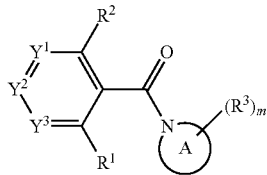

(In Scheme 1,

$X^1$, $X^2$, $X^3$, $R^1$, $R^2$, $R^3$ and m are defined as described before. One of $Y^1$, $Y^2$ and $Y^3$ is C—Br, C—I, or C—Cl, the others are independently N or C—$R^5$. One of $Z^1$, $Z^2$ and $Z^3$ is C—H, the others are independently N or C—$R^5$.)

Compounds of the general formula (I) can be prepared from anilines 1 or 2, or acids or esters 5 by several synthetic routes (Scheme 1). Most reactions needed in the build-up tolerate a wide range of functionalities, thus the sequence of many of the reactions steps is interchangeable. Optionally suitable protective functions can be introduced or be removed at any step of the synthesis. Anilines 1 or 2, nitriles 3 or 4, or acids/esters ($R^a$=H or $C_{1-6}$ alkyl) 5, 6 or 7 are known or can be prepared by methods known in the art. Suzuki couplings, the reaction with aryl or heteroaryl boronic acids or esters in the presence of a catalyst, such as tetrakis-(triphenylphosphine)-palladium, and in the presence of a base, such as potassium phosphate, in a solvent, such as toluene or N,N-dimethylformamide and in an inert atmosphere such as argon or nitrogen, in a temperature range preferably between room temperature and about 130° C. can be applied to transform anilines 1 into anilines 2, to transform nitriles 3 into nitriles 4, to transform acids or esters 6 into acids or esters 7 and to transform halo-amides 8 into compound of the general formula (I) (step a). Sandmeyer reactions, diazotization with sodium nitrite in the presence of a strong acid like hydrochloric or sulfuric acid followed by reaction with couprous cyanide optionally with a co-solvent like toluene or benzene preferably in a temperature range between 0° C. and 5° C. can convert anilines 1 or 2 into nitriles 3 or 4 (step b). Hydrolysis of nitriles 3 or 4 is performed by treatment with potassium hydroxide in a solvent like ethanol or 2-ethoxy-ethanol in a temperature range between about 80° C. and about 170° C. (optionally in an autoclave), by treatment with sulfuric acid in a temperature range between 140° C. and 180° C. as described by Lamm, G. *Ger. Offen.* (1977), DE 2538950 or by treatment with sulfuric acid and water at a temperature around 150° C. followed by further dilution with water and addition of a sodium nitrite solution at a temperature around 100° C. as described by Fuson, R. C.; Scott, S. L.; Lindsey, R. V., Jr. *Journal of the American Chemical Society* (1941), 63, 1679-82 (step c). In suitable cases, electrophilic aromatic halogenation, e.g. bromination in acetic acid can be used to introduce a halogen atom into acid or ester compounds 5 (step d). Amide formation starting from acids 6 or 7 (optionally prepared from $C_{1-6}$ alkyl esters 6 or 7 preferably by treatment with potassium hydroxide in a solvent like ethanol or 2-ethoxy-ethanol in a temperature range between room temperature and about 150° C.) with amines (III) is preferably being performed via acid chloride formation using e.g. oxalylchloride/N,N-dimethylformamide preferably at room temperature and optionally using dichloromethane as co-solvent followed by evaporation and reaction of the acid chlorides with the amines (III) in a solvent such as dichloromethane or N,N-dimethylformamide in the presence of a base like triethylamine preferably between 0° C. and room temperature (step e); alternatively, suitable amide coupling reagents can be used to couple acids 6 or 7 with amines (III), as e.g. O-(7-azabenzotriazol-1-yl)-1,1,3,3-tetramethyluronium hexafluorophosphate (HATU), and triethylamine, in a solvent like N,N-dimethylformamide preferably between 0° C. and room temperature (step e).

Scheme 2

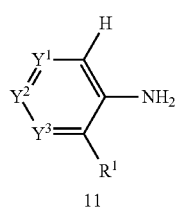
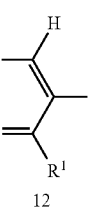
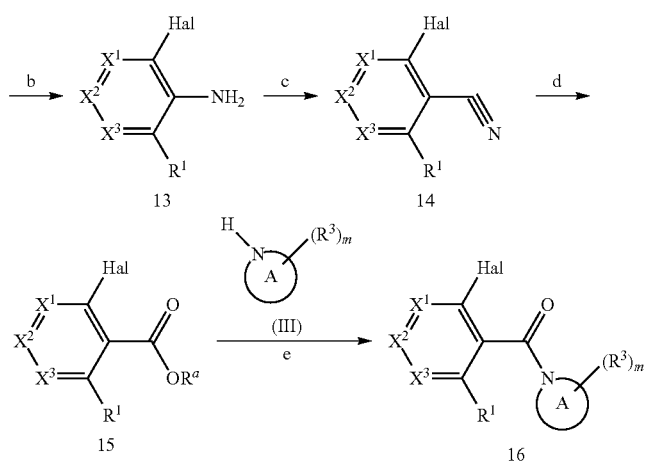

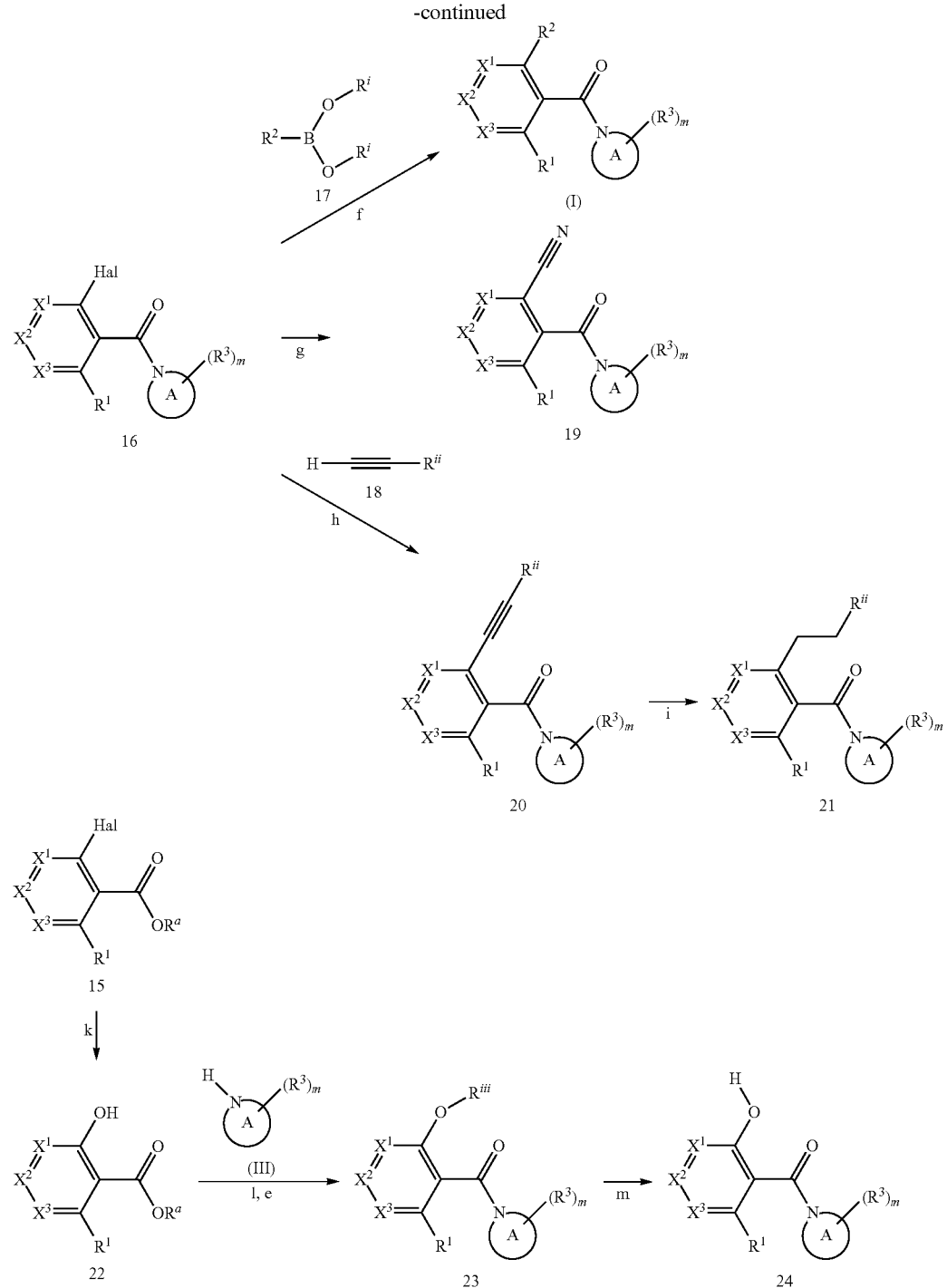

(In Scheme 2,

$X^1, X^2, X^3, Y^1, Y^2, Y^3, R^1, R^2, R^3$ and m are defined before.)
2-Halo-biarylamides 16 (Scheme 2) can be prepared from 3, 4, or 5-halo-anilines 11 by a reaction sequence closely analogous to the sequence described in Scheme 1. Halo-anilines 11 can be converted into biarylanilines 12 by Suzuki reactions as described for step a) in Scheme 1 (step a). Ortho halogenation can then be performed by methods well known in the art, e.g. using N-halosuccinimides in solvents like acetonitril or benzene preferably at reflux, bromine in acetic acid or iodine and silver sulfate in ethanol around room temperature (step b). Then, haloanilines 13 can be transformed into haloamides 16 in a sequence analogous to that described in Scheme 1 (2->4->7->(I)) by Sandmeyer reactions, nitril hydrolysis and amide formation ($R^a$=H; Hal=Cl, Br or I) (steps c, d, e). Substituted biaryles (I), 19, 20, and 21 (Scheme 2) can be prepared from halobiarylamides 16 by methods well known in the art. Suzuki couplings with boronic acids or esters 17 in the presence of a catalyst, such as tetrakis-(triphenylphosphine)-palladium, and in the presence of a base, such as potassium phosphate, in a solvent, such as toluene or N,N-dimethylformamide, in a temperature range preferably between about 70° C. and about 130° C. gives bi-aryl compounds (I) ($R^1$ is independently hydrogen, $C_{1-6}$ alkyl or both $R^i$s together form a $C_{1-6}$ alkylene group) (step f). Coupling with zinc cyanide in the presence of tetrakis-(triphenylphosphine)-palladium in a solvent, such as N,N-dimethylformamide, in a temperature range preferably between 130° C. and 150° C. gives cyano compounds 19 (step g). Sonogashira couplings with a reagent 18 containing a terminal acetylene function in the presence of copper(I) iodide, tetrakis-(triphenylphosphine)-palladium, tetrabutylammonium iodide and triethylamine, preferably in a solvent such as N,N-dimethylformamide, in a temperature range preferably between 50° C. and 80° C. gives aryl amides 20 carrying an acetylenic substituent (step h). The triple bond in the acetylenic substituent can optionally be reduced to a single bond by hydrogenation using e.g. $PtO_2$ as catalyst (step i).

is $C_{1-6}$ alkyl, halo $C_{1-6}$ alkyl, trimethylsilanyl $C_{1-6}$ alkyl, heteroalkyl or optionally substituted $C_{3-7}$ cycloalkyl $C_{1-6}$ alkyl). Optionally, $R^{ii}$ can be further modified: e.g. an $R^{ii}$ moiety carrying a hydroxy function can be reacted with a $C_{1-6}$ alkyl halide, $C_{1-6}$ alkyl methanesulfonate or $C_{1-6}$ alkyl tosylate in the presence of a base such as sodium hydride in a solvent such as N,N-dimethylformamide, in a temperature range preferably between 0° C. and 50° C. in order to attach an ether function. Alkyl ether compounds 23 ($R^{iii}$ is $C_{1-6}$ alkyl, halo $C_{1-6}$ alkyl or heteroalkyl) can be synthesized by reaction of halobiarylesters 15 ($R^a$ is methyl or ethyl, prepared from analogues 15 with $R^a$=H by methods well known in the art) with bis(pinacolato)diboron in a solvent like dioxane and in the presence of potassium acetate and bis(triphenylphosphine) palladium(II) chloride preferably between room temperature and about 100° C. giving a pinacolato-boron species which can be subsequently oxidized with 30% hydrogen peroxide in water in the presence of acetic acid to give phenol compounds 22 (step k). Phenols 22 can subsequently be alkylated with alkyl halides, alkyl methanesulfonates or alkyl tosylates in the presence of a base like sodium or potassium carbonate in a solvent like N,N-dimethylformamide to give the corresponding alkyl ether compounds; subsequent hydrolysis and coupling performed as described for step e, Scheme 1, then provides compounds 23 ($R^{iii}$ is $C_{1-6}$ alkyl, halo $C_{1-6}$ alkyl or heteroalkyl, steps 1, e). Compounds 23 ($R^{iii}$ is Me) can finally be converted into ortho hydroxy compounds 24 by reaction with boron-tribromide in dichloromethane preferable between 0° C. and room temperature (step m). Optionally, direct conversion of haloamides 16 into hydroxy compounds 24 can be performed via a boron intermediate under similar conditions to that described for the conversion of esters 15 into esters 22 (step k) and hydroxy compounds 24 can be alkylated selectively under conditions as described for step I providing ether compounds 23.

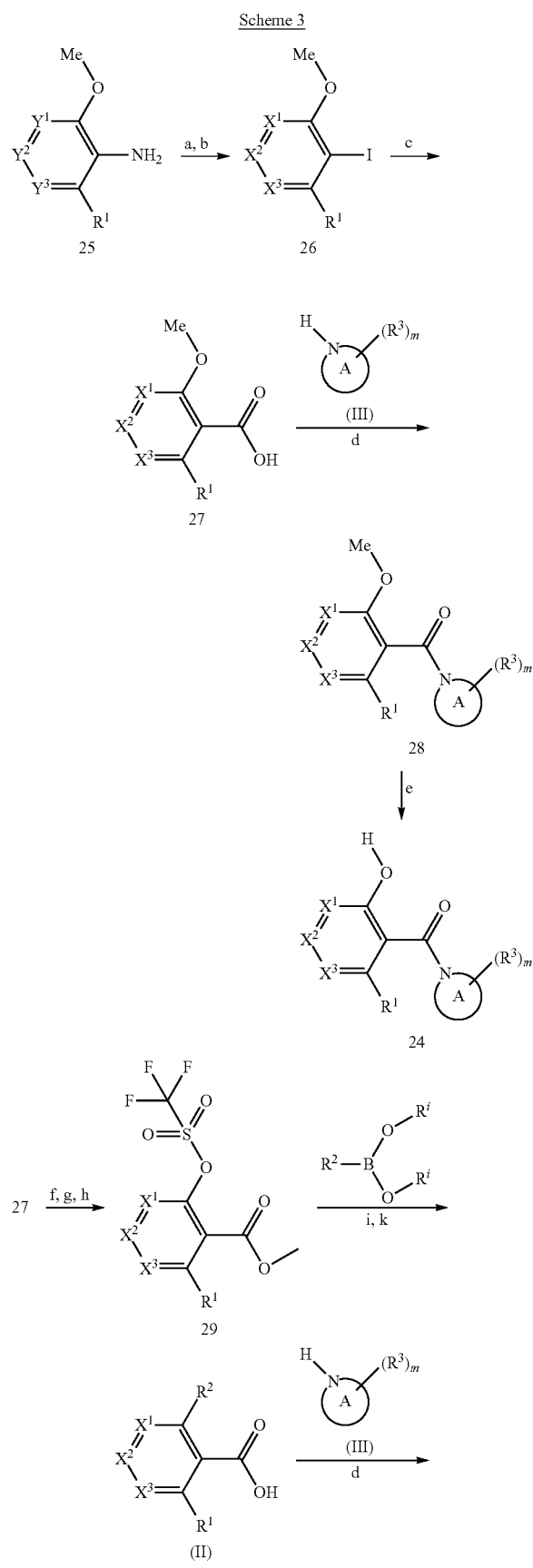

-continued

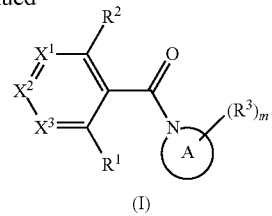
(I)

(In Scheme 3,

$X^1, X^2, X^3, Y^1, Y^2, Y^3, R^1, R^2, R^3$ and m are defined before. $R^i$ is independently hydrogen or $C_{1-6}$ alkyl, or both $R^i$ is together form a $C_{1-6}$ alkylene group.) 2-Hydroxy-biarylamides 24 (Scheme 3) can be prepared from 3, 4, or 5-halo-2-methoxy-anilines 25. Suzuki reactions as described for step a) in Scheme 1 and subsequent diazotization with sodium nitrite in the presence of a strong acid like hydrochloric or sulfuric acid followed by reaction with potassium iodide optionally with a co-solvent like toluene or benzene preferably in a temperature range between 0° C. and room temperature can convert 3, 4, or 5-halo-2-methoxy-anilines 25 into biaryl-iodides 26 (steps a, b). Treatment of iodides 26 with a base like n-butyl lithium in a solvent like tetrahydrofuran preferably at a temperature around −75° C. followed by reaction with dry $CO_2$ gas gives o-methoxy-biaryl carboxylic acids 27 (step c). o-Methoxy-biaryl carboxylic acids 27 can be coupled with amines (III) to give o-methoxy-biaryl carboxylic acid amides 28 using procedures similar to those described for step e, Scheme 1 (step d). Boron-tribromide in dichloromethane preferably between 0° C. and room temperature can be used to convert ortho-methoxy amides 28 into ortho-hydroxy amides 24 (step e). o-Methoxy-biaryl carboxylic acids 27 are converted into o-trifluoromethanesulfonyloxy-biphenyl-carboxylic acid methyl esters 29, first by a similar treatment with boron-tribromide in dichloromethane, followed by re-esterificiation (methanol, sulfuric acid, reflux) and trifluoromethane-sulfonate formation (trifluoromethanesulfonic anhydride and N-ethyldiisopropylamine in a solvent like dichloromethane preferably in a temperature range between −50° C. and 0° C.) (steps f, g, h). o-trifluoromethanesulfonyloxy-biphenyl-carboxylic acid methyl esters 29 undergo Suzuki couplings with boronic acids or esters 17 under conditions comparable to the ones described in Scheme 1, step a; subsequent saponification (treatment with lithium or potassium hydroxide in a solvent like ethanol, methanol, tetrahydrofuran or 2-ethoxy-ethanol and mixtures thereof in a temperature range between room temperature and about 150° C.) gives acids (II), which can be coupled with amines (III) to compounds (I) using procedures similar to those described for step e, Scheme 1 (steps i, k, d).

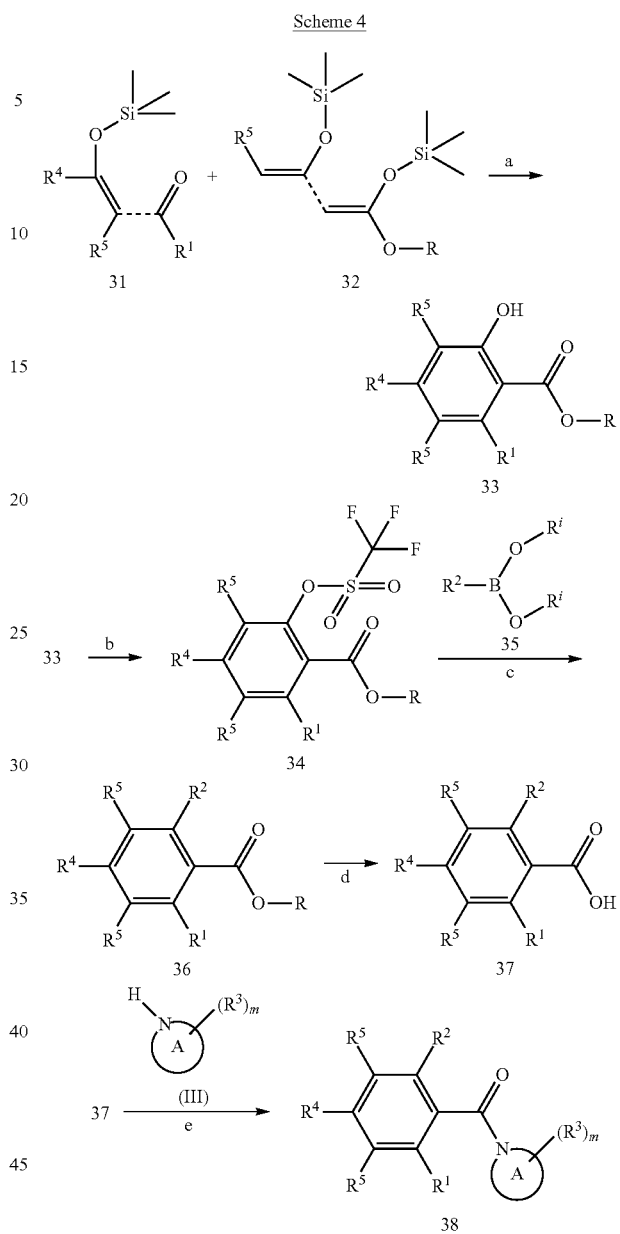

(In Scheme 4,

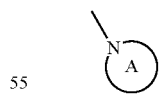

$R^1, R^2, R^3, R^4, R^5$ and m are defined before. R is $C_{1-6}$ alkyl. $R^i$ is independently hydrogen or $C_{1-6}$ alkyl, or both $R^i$'s together form a $C_{1-6}$ alkylene group.) Ortho hydroxy benzoic acid derivatives 33 can be prepared by a titanium tetrachloride catalyzed [3+3]cyclo-addition reaction between silylated dienes 32 and silylated enones 31 preferably in a solvent like dichloromethane and in a temperature range between −78° C. and room temperature [Reim, S.; Lau, M.; Langer, P. *Tetrahedron Letters* (2006), 47(38), 6903-6905] (Scheme 4, step a). Hydroxy derivatives 33 can be converted into triflates 34, e.g. using trifluoromethane sulfonic anhydride in pyridine in a temperature range between −78° C. and room temperature (step b). Suzuki reactions as described for step a) in Scheme 1 can then be used to convert triflates 34 into substituted benzoic acid derivatives 36 (step c). Saponification and amide coupling as described for the conversion of compounds 7 into compounds (I) (Scheme 1) gives then biarylamides 38 (steps d, e).

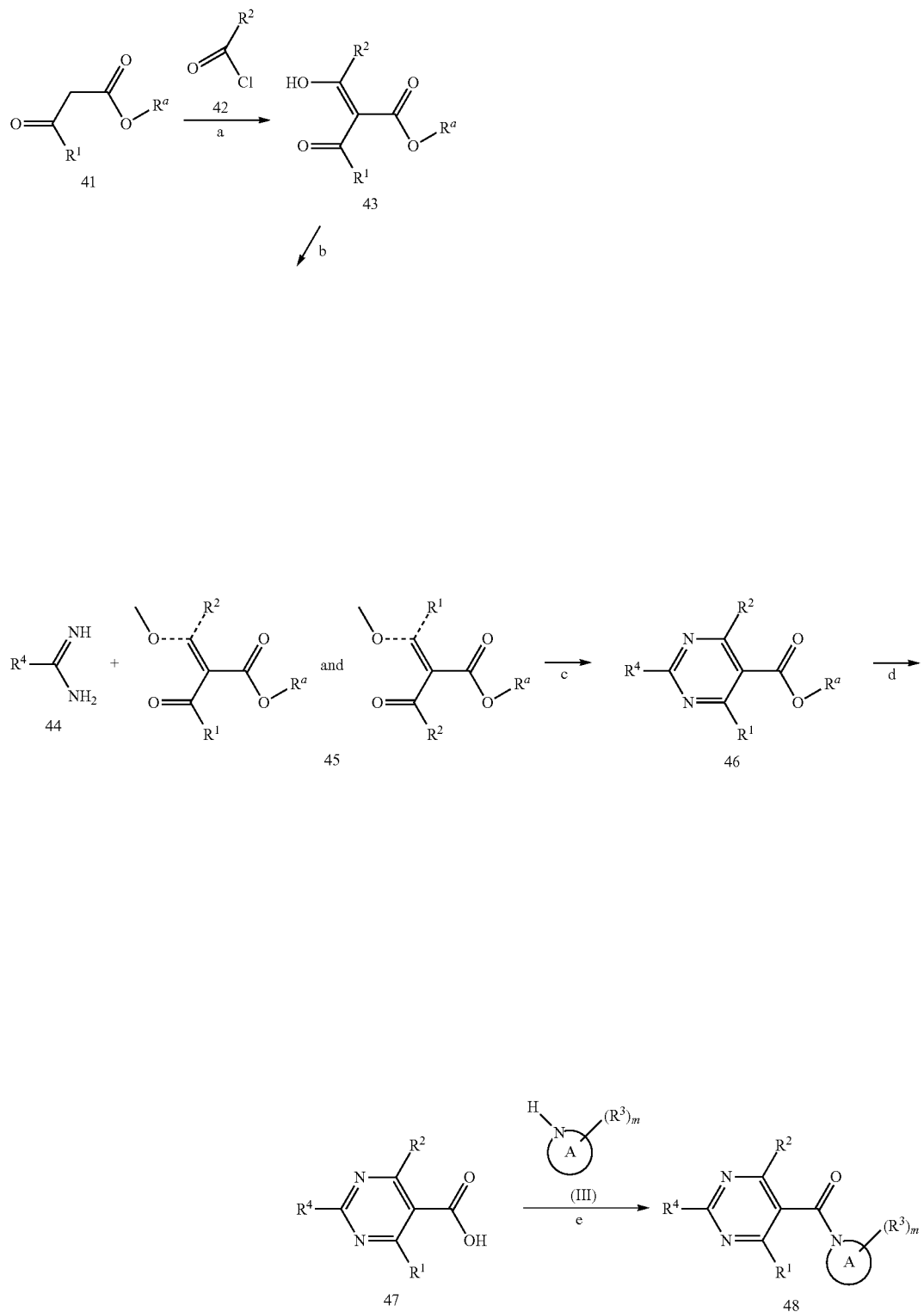

Scheme 5

(In Scheme 5,

$R^1$, $R^2$, $R^3$, $R^4$ and m are defined before.)

Acylated beta-keto esters 43 ($R^a$=$C_{1-6}$ alkyl) are known or can be prepared from beta-keto esters 41 by reaction with acid chlorides 42 in a solvent like dichloromethane in the presence of anhydrous magnesium chloride and pyridine preferably at room temperature (Scheme 5, step a). Methylation of acylated beta-keto esters 43 with trifluoro-methanesulfonic acid methyl ester preferably in a solvent such as acetonitrile and in the presence of a base like cesium carbonate around room temperature gives enol methyl ethers 45 as a mixture of isomers (step b). The isomeric mixture 45 can be condensed with amidines 44 preferably in a solvent like ethanol (sodium tert-butoxide is used to liberate the free amidines from more readily available amidine hydrochlorides) in a temperature range between room temperature and the reflux temperature of the solvent to give pyrimidine compounds 46 [McCombie, S. W.; Tagat, J. R.; Vice, S. F.; Lin, S.-I.; Steensma, R.; Palani, A.; Neustadt, B. R.; Baroudy, B. M.; Strizki, J. M.; Endres, M.; Cox, K.; Dan, N.; Chou, C.-C. *Bioorganic & Medicinal Chemistry Letters* (2003), 13(3), 567-571] (step c). Pyrimidine compounds 46 can be converted into final compounds 48 in a sequence fully analogous to that described in Scheme 1 (transformation of compounds 7 into compounds (I)).

Scheme 6

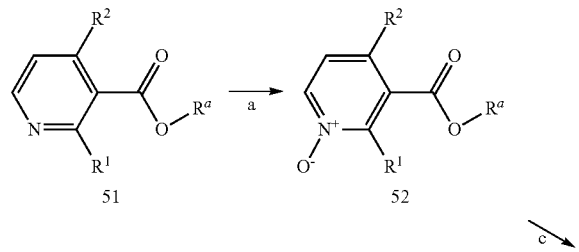

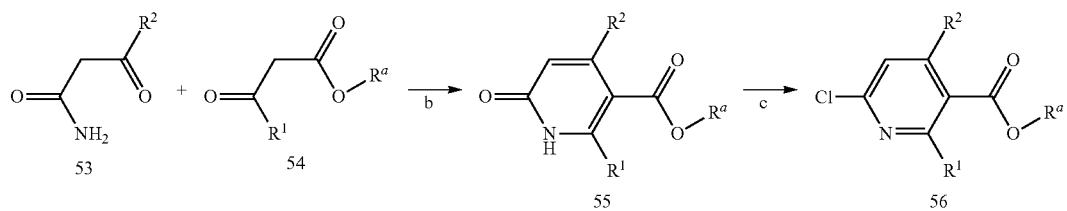

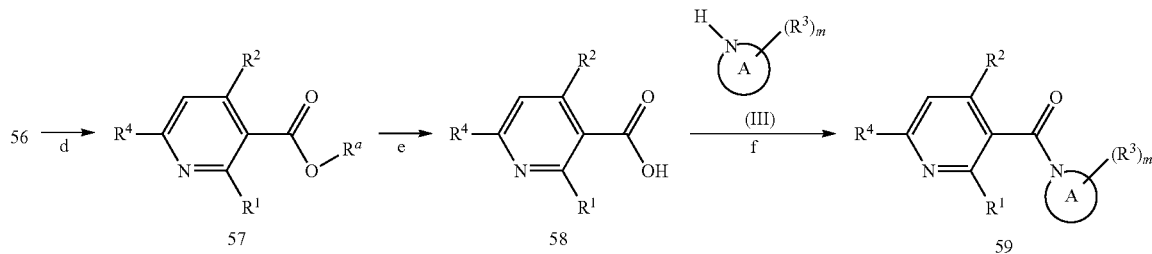

(In Scheme 6,

$R^1$, $R^2$, $R^3$, $R^4$ and m are defined before.) Pyridine N-oxides 52 can be prepared from pyridines 51 ($R^a$ is $C_{1-6}$ alkyl) e.g. by reaction with meta-chloroperbenzoic acid in a solvent like dichloromethane (Scheme 6, step a). Pyridones 55 can be prepared from beta keto amides 53 and beta keto esters 54 ($R^a$=$C_{1-6}$ alkyl) by treatment with polyphosphoric acid at elevated temperature as described by Kato, T.; Sato, M.; Noda, M. Itoh, T. *Chemical & Pharmaceutical Bulletin* (1980), 28(7), 2244-7 (step b). Pyridine N-oxides 52 and pyridones 55 can be transformed into chloropyridines 56 by treatment with $POCl_3$ or a mixture of $POCl_3$ and $PCl_5$ at temperatures between about 100° C. and the reflux temperature of the $POCl_3$ (step c). Suzuki couplings with boronic acids and esters as described e.g. for step a in Scheme 1 can be used to transform chloropyridines 56 into aryl or heteroaryl substituted pyridines 57 (step d). The transformation of substituted pyridines 57 into pyridine amides 59 follows then a sequence as described for the transformation of compounds 7 into compounds (I) in Scheme 1 (steps e, f).

Scheme 7

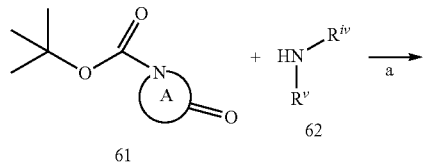

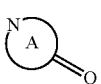

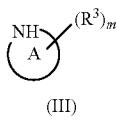

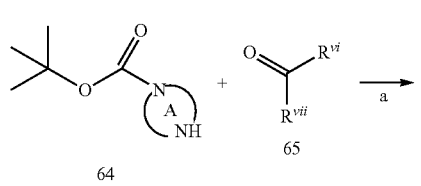

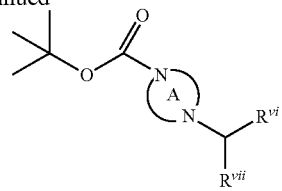

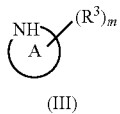

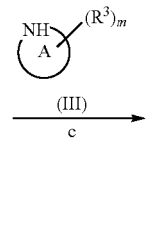

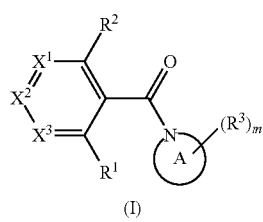

(In Scheme 7,

m, $X^1$, $X^2$, $X^3$, $R^1$, $R^2$, and $R^3$ are as defined before.

is heterocyclyl, which is a non-aromatic mono-cyclic radical of four to eight ring atoms, in which one ring atom is a nitrogen atom, the remaining ring atoms being carbon atoms; one of these carbon atoms is bearing a carbonyl group, said carbon atom is not directly bonded to the nitrogen atom.

is heterocyclyl, which is a non-aromatic mono-cyclic radical of four to eight ring atoms, in which two ring atoms are nitrogen atoms, the remaining ring atoms being carbon atoms. $R^{iv}$ and $R^v$ are independently hydrogen, $C_{1-6}$ alkyl, heteroalkyl, optionally substituted $C_{3-7}$ cycloalkyl or optionally substituted heterocyclyl or

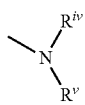

is optionally substituted heterocyclyl.

is $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, optionally substituted $C_{3-7}$ cycloalkyl, optionally substituted $C_{3-7}$ cycloalkyl $C_{1-6}$ alkyl, optionally substituted phenyl $C_{1-6}$ alkyl, optionally substituted heteroaryl $C_{1-6}$ alkyl, optionally substituted heterocyclyl or optionally substituted heterocyclyl $C_{1-6}$ alkyl.)

Secondary amines (III) (Scheme 7) are known, can be prepared by the methods known in the art or the methods described in the examples or can be prepared e.g. by reductive amination of ketones 61 with secondary amines 62 or by reductive amination of secondary amines 64 with ketones 65 e.g. by using sodium triacetoxy-borohydride, sodium cyanoborohydride or borane-pyridine complex as reagents in the presence of acetic acid and potentially a base, such as trietylamine, in a solvent, such as 1,2-dichloro-ethane, at temperatures around room temperature (step a). Such a reductive amination leads to Boc-protected adducts 63 or 66 which are subsequently deprotected by well established procedures as e.g. trifluoroacetic acid with or without an additional solvent or alcoholic hydrogen chloride to give secondary amines (III) (step b). Biaryl carboxylic acids (II) can then be coupled with secondary amines (III) to amides (I) i) by transformation of the biaryl carboxylic acids (II) into the corresponding acid chlorides, preferably by reaction with oxalyl chloride and a catalytic amount of N,N-dimethylformamide and optionally using dichloromethane as co-solvent followed by evaporation and reaction of the acid chlorides with secondary amines (III) in a solvent like dichloromethane or NAN-dimethylformamide in the presence of a base like triethylamine preferably between 0° C. and room temperature or ii) by suitable amide coupling reactions, such as using of O-(7-azabenzotriazol-1-yl)-1,1,3,3-tetramethyluronium hexafluorophosphate (HATU), triethylamine, in N,N-dimethylformamide preferably between 0° C. and room temperature (step c). During these coupling reactions, OH-functions potentially present in secondary amines (III) can potentially be protected by a suitable protective group which is removed after the coupling reaction or at a later stage of the synthesis.

Scheme 8

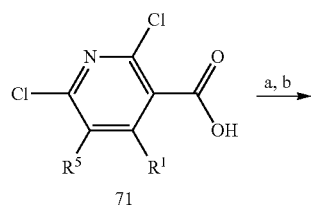

71

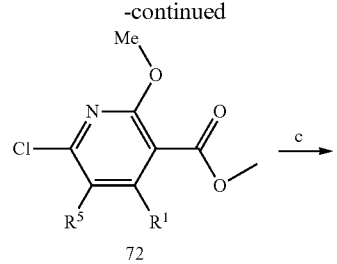

72

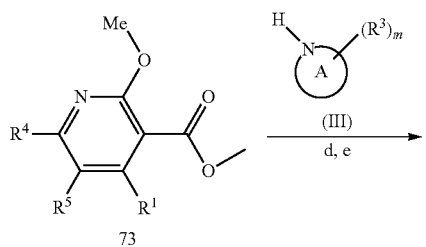

73

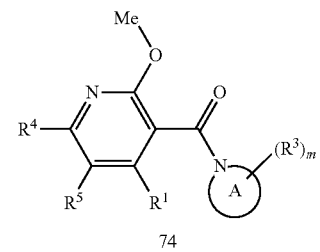

74

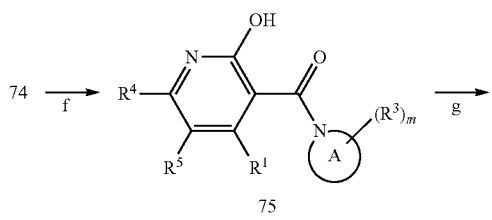

75

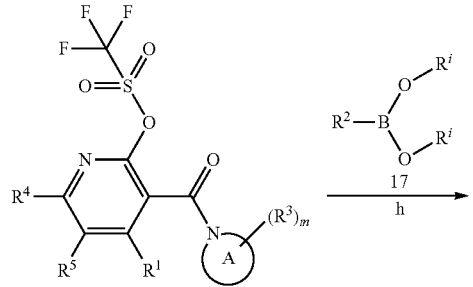

76

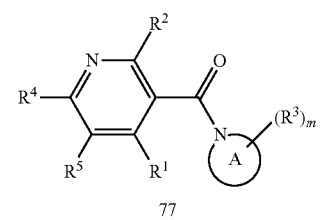

77

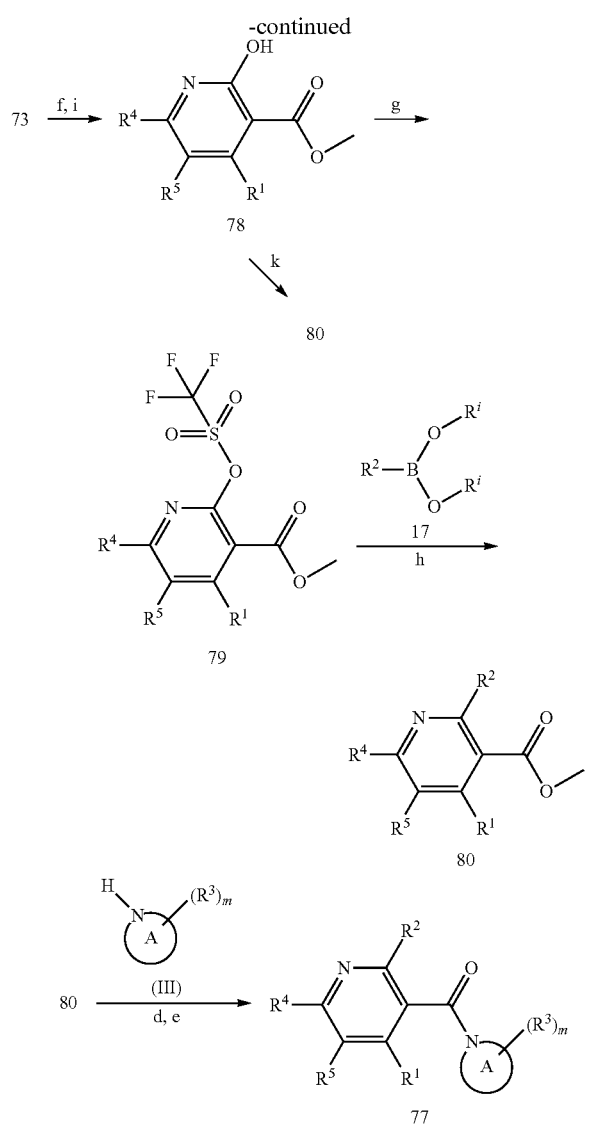

$R^1$, $R^2$, $R^3$, $R^4$, $R^5$ and m are defined before. $R^i$ is independently hydrogen or $C_{1-6}$ alkyl, or both $R^i$'s together form a $C_{1-6}$ alkylene group.)

Aryl-pyridine amides 74, 75 and 77 can be prepared from dichloropyridine carboxylic acids 71 (Scheme 8) by several synthetic routes. The dichloropyridine carboxylic acids 71 can be esterified (e.g. using iodomethane, potassium carbonate in N,N-dimethylformamide preferably at room temperature) and then reacted with sodium methoxide in dichloromethane preferably between 0° C. and room temperature to give 6-chloro-2-methoxy-nicotinic acid methyl esters 72 (steps a, b). Suzuki reactions as described for step a) in Scheme 1 transform 6-chloro-2-methoxy-nicotinic acid methyl esters 72 into methoxy-bi-aryl esters 73 (step c). Subsequent saponification (treatment with lithium or potassium hydroxide in a solvent like ethanol, methanol, tetrahydrofuran or 2-ethoxy-ethanol and mixtures thereof in a temperature range between room temperature and about 150° C.) and coupling with amines (III) gives methoxy-pyridine amides 74 using procedures similar to those described for step e, Scheme 1 (steps d, e). Treatment of methoxy-pyridine amides 74 with boron tribromide in dichloromethane preferable between 0° C. and room temperature gives hydroxy-pyridine amides 75 (step f); similar treatment of methoxy-bi-aryl esters 73 followed by esterification (e.g. using methanol, sulfuric acid at reflux) gives esters 78 (steps f, i). Hydroxy-pyridine amides 75 or esters 78 can be converted into trifluoromethanesulfonates 76 or 79 (step g, see Scheme 3, step h); alkylation of hydroxy-pyridine esters 78 with a suitable alkyl halide in the presence of a base like cesium or potassium carbonate in a solvent like acetonitrile, N,N-dimethylformamide or tetrahydrofuran gives esters 80 with $R^2$ being and O-alkyl function (step k). Suzuki reactions as described for step a) in Scheme 1 can be used to convert triflates 76 or 79 into substituted bi-aryl amides or esters 77 or 80 (step h). Saponification of esters 80 (treatment with lithium or potassium hydroxide in a solvent like ethanol, methanol, tetrahydrofuran or 2-ethoxy-ethanol and mixtures thereof in a temperature range between room temperature and about 150° C.) and coupling with amines (III) using procedures similar to those described for step e, Scheme 1, gives aryl-pyridine amides 77 (steps d, e).

(In Scheme 8,

),

Scheme 9

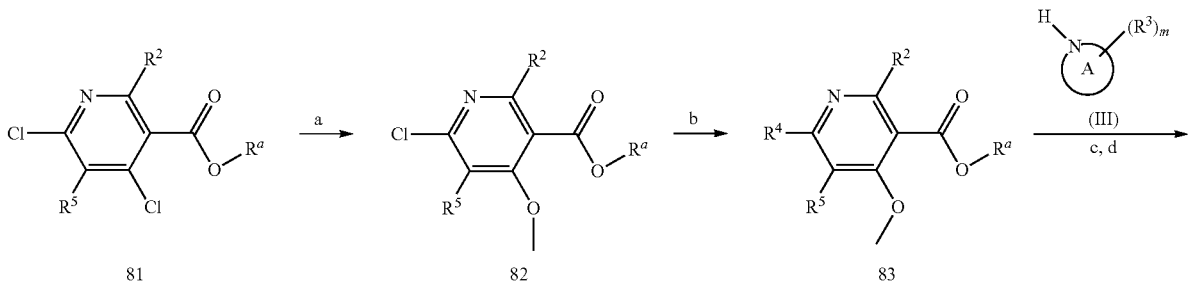

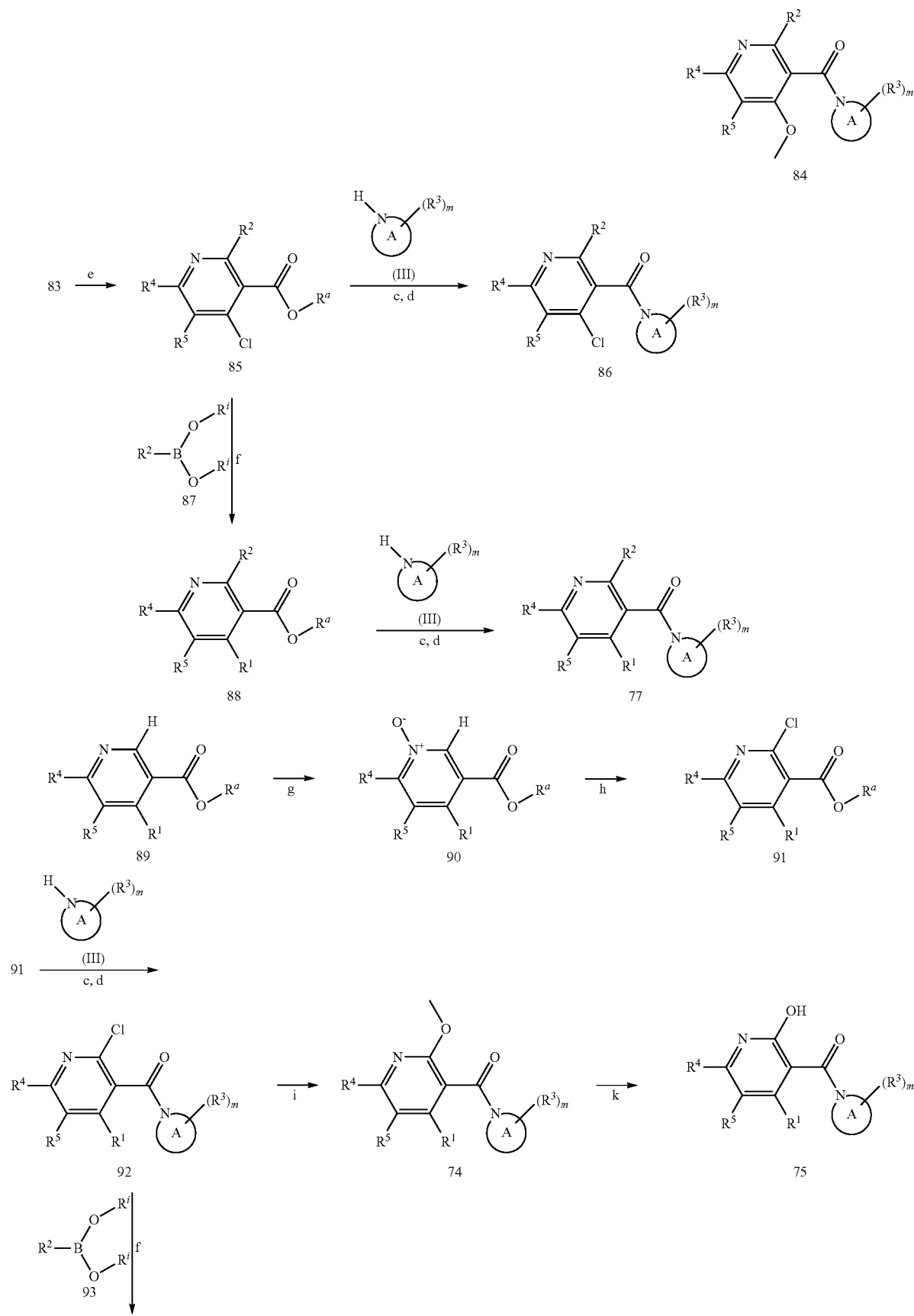

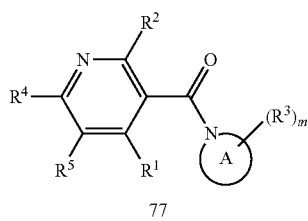

77

(In Scheme 9,

$R^1$, $R^2$, $R^3$, $R^4$, $R^5$ and m are defined before. $R^i$ is independently hydrogen or $C_{1-6}$ alkyl, or both $R^i$s together form a $C_{1-6}$ alkylene group. $R^a$ is $C_{1-6}$ alkyl.)

Alkyl dichloropyridine carboxylates 81 (Scheme 9) undergo selective substitution of the chloro atom ortho to the ester function when treated with sodium methylate in a solvent like tetrahydrofuran preferably around room temperature [Hutchison, A.; Y., Jun; L., K.; Maynard, G.; Chenard, B. L.; Liu, N.; Guo, Q.; Guo, Z.; Hrnciar, P. PCT Int. Appl. (2004), WO2004043925A2] (step a). Suzuki reactions as described for step a) in Scheme 1 transform chloro-methoxy-pyridine carboxylates 82 into methoxy-bi-aryl esters 83 (step b). Subsequent saponification (treatment with lithium or potassium hydroxide in a solvent like ethanol, methanol, tetrahydrofuran or 2-ethoxy-ethanol and mixtures thereof in a temperature range between room temperature and about 150° C.) and coupling with amines (III) gives methoxy-pyridine amides 84 using procedures similar to those described for step e, Scheme 1 (steps c, d). Treatment of methoxy-bi-aryl esters 83 with phosphorus oxychloride and N,N-dimethylformamide preferably at a temperature around 80° C. gives chloro-bi-aryl esters 85 [Hutchison, A.; Y., Jun; L., K.; Maynard, G.; Chenard, B. L.; Liu, N.; Guo, Q.; Guo, Z.; Hrnciar, P. PCT Int. Appl. (2004), WO2004043925A2] (step e). Chloro-bi-aryl esters 85 can be saponified and coupled with amines (III) as described above (steps c, d) to give chloro-biaryl-amides 86, or can undergo Suzuki reactions as described for step a) in Scheme 1 with boronic acids or esters 87 to give substituted bi-aryl esters 88 (step f). Substituted bi-aryl esters 88 can be saponified and coupled with amines (III) as described above to give biarylamides 77 (steps c, d). Oxidation of in ortho position not substituted pyridine esters 89 with meta-chloro-perbenzoic acid preferably in dichloromethane at room temperature gives N-oxides 90 (step g). Treatment of N-oxides 90 with phosphorus oxychloride preferably between about 50° C. and about 100° C. gives chloro-pyridine esters 91 (step h). Chloro pyridine esters 91 can be saponified and coupled with amines (III) as described above (steps c, d) to give chloro-pyridine amides 92. Treatment of chloro-pyridine amides 92 with sodium methoxide in methanol preferably between room temperature and reflux converts chloro-pyridine amides 92 into methoxy-pyridine amides 74 (step i). Treatment of methoxy-pyridine amides 74 with boron tribromide in dichloromethane preferable between 0° C. and room temperature gives hydroxy-pyridine amides 75 (step k). Suzuki reactions, treatment of chloro-pyridine amides 92 with boronic acids or esters 93 under conditions as described for step a) in Scheme 1 give biarylamides 77 (step f).

In addition to the reaction steps explicitly described in schemes 1-9, optionally, additional well established synthetic structural modification can be applied to any substituent at any stage of the syntheses described, as e.g. introduction and removal of protective groups.

As described above, the compounds of formula (I) are CCR-2 receptor antagonists, with some antagonist activity also at CCR-3 and CCR-5. These compounds consequently prevent migration of various leukocyte populations through the blockade of CCR-2 stimulation. They therefore can be used for the treatment and/or prevention of inflammatory and/or allergic diseases in a human being, such as peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis and/or burns/ulcers in Diabetes/CLI, and asthma.

Prevention and/or treatment of inflammatory diseases, particularly peripheral arterial occlusive diseases or atherothrombosis is the preferred indication.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment and/or prophylaxis of inflammatory and/or allergic diseases in a human being, particularly as therapeutically active substances for the treatment and/or prophylaxis of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and allergy, asthma.

The invention also relates to the use of compounds as described above for the preparation of medicaments for the therapeutic and/or prophylactic treatment of inflammatory and/or allergic diseases in a human being, particularly for the therapeutic and/or prophylactic treatment of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and asthma. Such medicaments comprise a compound as described above.

The invention also comprises a method for the treatment of a disease treatable by a CCR-2 receptor antagonist, CCR-3 recetor antagonist or CCR-5 receptor antagonist, comprising administering the compound of claim 1 to a human being. The method of claim 21, wherein the disease is selected from the group consisting of peripheral arterial occlusive disease, critical limb ischemia, vulnerable atherosclerotic plaque patients, unstable angina, congestive heart failure, left ventricular hypertrophy, ischemia reperfusion injury, stroke, cardiomyopathy, restenosis, rheumatoid arthritis, diabetic nephropathy, irritable Bowel Disease, Crohns' disease, multiple sclerosis, neuropathic pain, atherothrombosis, burns/ulcers in Diabetes/CLI, and allergy, asthma.

The invention also relates to the process and the intermediates for manufacturing the compounds of formula (I) as well as the process for manufacturing the intermediates.

CCR-2 receptor antagonistic activity by the compounds of the present invention can be demonstrated by the following assays.

Receptor Binding Assay

Binding assays were done with membranes from CHOK1-CCR2B-A5 cells (Euroscreen) stably overexpressing the human CCR2B.

Membranes were prepared by homogenizing the cells in 10 mM Tris pH 7.4, 1 mM EDTA, 0.05 mM benzamidine, leupeptin 6 mg/L and separating the debris at 1000 g. The membranes were then isolated at 100000 g in 50 mM Tris pH 7.4, $MgCl_2$ 10 mM, EGTA 1 mM, glycerol 10%, benzamidine 0.05 mM, leupeptine 6 mg/l.

For binding, CCR2 antagonist compounds were added in various concentrations in 50 mM HEPES pH 7.2, 1 mM $CaCl_2$, 5 mM $MgCl_2$, 0.5% BSA, 0.01% $NaN_3$, together with 100 pM $^{125}$I-MCP-1 (PerkinElmer, 2200 Ci/mmol) to about 5 fMol CCR2 membranes and incubated for 1 hour at room temperature. For unspecific control 57.7 nM MCP-1 (R&D Systems or prepared at Roche) was added. Membranes were harvested through GF/B (glass fiber filter; PerkinElmer) plates, equilibrated with 0.3% polyethylenimine, 0.2% BSA, air dried and binding was determined by counting in a top-counter (NXT Packard). Specific binding was defined as total binding minus nonspecific binding and typically represents about 90-95% of the total binding. Antagonist activity is indicated as inhibitor concentration required for 50% inhibition ($IC_{50}$) of specific binding.

Calcium Mobilization Assay

CHOK1-CCR2B-A5 cells (from Euroscreen) stably overexpressing the human chemokine receptor 2 isoform B were cultured in Nutrient Hams F12 medium supplemented with 5% FBS, 100 U/ml penicillin, 100 µg/ml streptomycin, 400 µg/ml G418 and 5 µg/ml puromycin.

For the assay cells were grown overnight in 384-well black clear flat bottom polystyrene plates (Costar) at 37° C. at 5% $CO_2$. After washing with DMEM, 20 mM Hepes, 2.5 mM probenecid, 0.1% BSA (DMEM assay buffer) cells were loaded with 4 µM Fluo-4 in the same DMEM assay buffer for 2 hours at 30° C. Excess dye was removed and cells were washed with DMEM assay buffer. 384-well compound plates were prepared with DMEM assay buffer/0.5% DMSO with or without various concentrations of test compounds. Usually compounds were tested for agonist and antagonist activity.

Test compounds were added to the assay plate and agonist activity was monitored as fluorescence for 80 seconds with a FLIPR (488 nm excitation; 510-570 nm emission; Molecular Devices). After 20-30 min. of incubation at 30° C., 20 nM MCP-1 (R&D; Roche) was added and fluorescence was monitored again for 80 seconds. Increases in intracellular calcium are reported as maximum fluorescence after agonist exposure minus basal fluorescence before exposure. Antagonist activity is indicated as inhibitor concentration required for 50% inhibition of specific calcium increases.

The compounds of general formula (I) exhibit $IC_{50}$ values in the Ca mobilisation assay or in the receptor binding assay of 0.1 nM to 10 µM, preferably 1 nM to 1.5 µM for CCR2. The following table shows measured values in the calcium mobilization assay for some selected compounds of the present invention.

| Example | IC50 (µM) |
| --- | --- |
| 1 | 0.060 |
| 2 | 0.021 |
| 6 | 0.43 |
| 7 | 0.15 |
| 9 | 0.009 |
| 10 | 0.039 |
| 13 | 0.19 |
| 14 | 0.048 |
| 16 | 0.31 |
| 18 | 0.49 |
| 19 | 0.99 |
| 22 | 0.055 |
| 24 | 0.27 |
| 27 | 0.021 |
| 28 | 0.079 |
| 29 | 0.15 |
| 30 | 0.067 |
| 39 | 0.089 |
| 40 | 0.22 |
| 42 | 0.24 |
| 43 | 0.48 |
| 44 | 0.076 |
| 45 | 0.048 |
| 46 | 0.122 |
| 47 | 0.012 |
| 48 | 0.016 |
| 50 | 0.082 |
| 51 | 0.017 |
| 53 | 0.011 |

The compounds of formula (I) and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage, a therapeutically effective amount, of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 300 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-100 mg, of a compound of formula (I).

The following Examples serve to illustrate the present invention in more detail. They are, however, not intended to limit its scope in any manner.

EXAMPLES

Abbreviations

AcOH=Acetic acid, BOC=t-Butyloxycarbonyl, BuLi=Butyllithium, CDI=1,1-carbonyldiimidazole, $CH_2Cl_2$=dichloromethane, DCE=1,2-dichloroethane, DIBALH Di-i--butylaluminium hydride, DCC=N,N'-Dicyclohexylcarbodiimide, DMA N,N-Dimethylacetamide, DMAP=4-Dimethylaminopyridine, DMF=N,N-Dimethylformamide, EDCI=N-(3-Dimethylaminopropyl)-N'-ethylcarbodiimide hydrochloride, EtOAc=Ethylacetate, EtOH=Ethanol, $Et_2O$=Diethylether, $Et_3N$=Triethylamine, eq=Equivalents, HATU=O-(7-azabenzotriazol-1-yl)-1,1,3,3-tetramethyluronium hexafluorophosphate, HOBT=1-Hydroxybenzo-triazole, Huenig's base=iPr$_2$NEt=N-Ethyl diisopropylamine, LAH=Lithium aluminium hydride, LDA=Lithium diisopropylamide, LiBH$_4$=Lithium borohydride, MeOH=Methanol, NaI=Sodium iodide, Red-Al=Sodium bis(2-methoxyethoxy) aluminium hydride, RT=room temperature, TBDMSCl=t-Butyldimethylsilyl chloride, TFA=Trifluoroacetic acid, THF=Tetrahydrofuran, quant=quantitative.

General Remarks

All reactions were performed under argon.

Intermediate 1

(4-Bromo-2,6-dimethyl-phenyl)-(4-pyrrolidin-1-yl-piperidin-1-yl)-methanone

A suspension of 0.344 g (1.5 mmol) 4-bromo-2,6-dimethyl-benzoic acid [Fuson, R. C.; Scott, S. L.; Lindsey, R. V., Jr. *Journal of the American Chemical Society* (1941), 63, 1679-82] in 5 ml of $CH_2Cl_2$ was treated at RT with two drops of DMF; then, a solution of 0.14 ml=0.21 g (1.6 mmol) of oxalyl chloride in 3 ml of $CH_2Cl_2$ was added drop by drop below 25° C. and the reaction mixture was stirred of 1 hour. After removal of the solvents by evaporation in a high vacuum, the residue was dissolved again in 10 ml of $CH_2Cl_2$ and the solution cooled down to 0° C.; then, 0.42 ml=0.30 g (3.0 mmol) of $Et_3N$ was added while stirring, followed by 0.23 g (1.5 mmol) of 4-pyrrolidin-1-yl-piperidine. The reaction mixture was subsequently warmed up to RT. After 60 hours, it was poured into crashed ice and extracted twice with $CH_2Cl_2$; the organic phases were washed with water, dried over magnesium sulfate, filtered and evaporated. The residue was purified by flash column chromatography ($CH_2Cl_2$/MeOH 1:0 to 95:5) to give 0.42 g (76%) of the title compound as light yellow oil. MS: 365.0 (MH$^+$, 1 Br).

Intermediate 2

(3-Bromo-2-methyl-phenyl)-(4-pyrrolidin-1-yl-piperidin-1-yl)-methanone 0.22 g (1.0 mmol) of 3-bromo-2-methyl-benzoic acid was dissolved in 10 ml of DMF and the solution was treated with 0.38 g (1.0 mmol) of HATU. Then, 0.42 ml=0.30 g (3.0 mmol) of $Et_3N$ was added and after 30 min, a solution of 0.16 g (1.0 mmol) of 4-pyrrolidin-1-yl-piperidine in 5 ml of DMF. After 3 hours, the reaction mixture was poured into crashed ice and extracted three times with $CH_2Cl_2$; the organic phases were washed with water, dried over magnesium sulfate, filtered and evaporated. The residue was purified by flash column chromatography ($CH_2Cl_2$/MeOH 1:0 to 9:1) to give 0.33 g (95%) of the title compound as light red solid. MS: 351.2 (MH$^+$, 1 Br).

Intermediate 3

Benzoic acid (S)-1-piperidin-4-yl-pyrrolidin-2-ylmethyl ester

A) 4-((S)-2-Hydroxymethyl-pyrrolidin-1-yl)-piperidine-1-carboxylic acid tert-butyl ester A solution of 10.0 g (50.2 mmol) of 4-oxo-piperidine-1-carboxylic acid tert-butyl ester and 6.00 ml=6.15 g (60.2 mmol) of (S)-(−)-pyrrolidin-2-yl-methanol in 100.0 ml of EtOH was treated with 100.0 ml of 1,2-dichloroethane, followed by 7.53 ml (60.2 mmol) of borane-pyridine complex (8 molar). Then, 7.46 ml=7.84 g (130.5 mmol) of acetic acid was added to this solution. After stirring at RT for 16 hours, the reaction mixture was poured into crashed ice; then, the pH was adjusted to 9-10 with sodium carbonate solution and the mixture was extracted twice with EtOAc; the combined organic phases were washed with water, dried over MgSO$_4$, filtered and evaporated. The residue was purified by flash column chromatography ($CH_2Cl_2$/MeOH 1:0 to 9:1) to give 10.4 g (73%) of the title compound as light yellow oil. MS: 285.1 (MH$^+$).

B) 4-((S)-2-Benzoyloxymethyl-pyrrolidin-1-yl)-piperidine-1-carboxylic acid tert-butyl ester 3.35 g (11.8 mmol) of 4-((S)-2-hydroxymethyl-pyrrolidin-1-yl)-piperidine-1-carboxylic acid tert-butyl ester was dissolved in 55 ml of THF at RT and treated with 0.57 g (13.0 mmol) of sodium hydride (55% in mineral oil). 1.68 ml=2.03 g (14.1 mmol) of benzoyl chloride was added drop by drop and stirring continued for 2 hours. The reaction mixture was then poured into crashed ice and extracted three times with EtOAc; the organic phases were washed with water, dried over magnesium sulfate, filtered and evaporated. The residue was purified by flash column chromatography ($CH_2Cl_2$/MeOH 1:0 to 95:5) to give 2.80 g (61%) of the title compound as yellow oil. MS: 389.3 ($MH^+$).

C) Benzoic acid (S)-1-piperidin-4-yl-pyrrolidin-2-ylmethyl ester

To a solution of 2.78 g (7.2 mmol) of 4-((S)-2-benzoyloxymethyl-pyrrolidin-1-yl)-piperidine-1-carboxylic acid tert-butyl ester in 80 ml of $CH_2Cl_2$ was added 5.83 ml of TFA (90% in water) drop by drop. After 16 hours, the reaction mixture was poured into crashed ice; then, the pH was adjusted to 9-10 with sodium carbonate solution and the mixture was extracted three times with $CH_2Cl_2$; the organic phases were washed with water, dried over magnesium sulfate, filtered and evaporated. The residue was purified by flash column chromatography [$CH_2Cl_2$ (sat. with $NH_3$) and MeOH 1:0 to 9:1] to give 1.96 g (95%) of the title compound as yellow oil. MS: 289.1 ($MH^+$).

Intermediate 4

(4-Bromo-2,6-dimethyl-phenyl)-[4-((S)-2-hydroxymethyl-pyrrolidin-1-yl)-piperidin-1-yl]-methanone A) Benzoic acid (S)-1-[1-(4-bromo-2,6-dimethyl-benzoyl)-piperidin-4-yl]-pyrrolidin-2-ylmethyl ester In analogy to the procedure described for intermediate 1, 4-bromo-2,6-dimethyl-benzoic acid [Fuson, R. C.; Scott, S. L.; Lindsey, R. V., Jr. *Journal of the American Chemical Society* (1941), 63, 1679-82] was converted into its acid chloride and subsequently reacted with benzoic acid (S)-1-piperidin-4-yl-pyrrolidin-2-ylmethyl ester (intermediate 3) to give the title compound as yellow oil. MS:=499.1 ($MH^+$, 1 Br).

B) (4-Bromo-2,6-dimethyl-phenyl)-[4-((S)-2-hydroxymethyl-pyrrolidin-1-yl)-piperidin-1-yl]-methanone To a solution of 2.20 g (4.4 mmol) of benzoic acid (S)-1-[1-(4-bromo-2,6-dimethyl-benzoyl)-piperidin-4-yl]-pyrrolidin-2-ylmethyl ester in 120 ml of THF/MeOH (1:1) was added 11.0 ml (11.0 mmol) of lithium hydroxide solution (1 molar in water) drop by drop and the reaction mixture was then heated up to 50° C. After 2 hours, the solvents were evaporated and the residue poured into crashed ice and extracted twice with $CH_2Cl_2$; the organic phases were washed with water, dried over magnesium sulfate, filtered and evaporated. The residue was purified by flash column chromatography ($CH_2Cl_2$/MeOH 1:0 to 9:1) to give 1.19 g (68%) of the title compound as light yellow oil. MS: 395.2 ($MH^+$, 1 Br).

Intermediate 5

4,6-Dimethyl-2-(3-trifluoromethyl-phenyl)-pyrimidine-5-carboxylic acid

A) 4,6-Dimethyl-2-(3-trifluoromethyl-phenyl)-pyrimidine-5-carboxylic acid ethyl ester A solution of 5.31 g (23.6 mmol) 3-trifluoromethyl-benzamidine HCl in 60 ml EtOH was treated with 2.34 g (23.6 mmol) of sodium tert-butoxide. After 4 min, 4.40 g (23.6 mmol) of crude (E,Z)-2-acetyl-3-methoxy-but-2-enoic acid ethyl ester [McCombie, S. W.; Tagat, J. R.; Vice, S. F.; Lin, S.-I.; Steensma, R.; Palani, A.; Neustadt, B. R.; Baroudy, B. M.; Strizki, J. M.; Endres, M.; Cox, K.; Dan, N.; Chou, C.-C. *Bioorganic & Medicinal Chemistry Letters* (2003), 13(3), 567-571] in 40 ml of EtOH was added. Then, the reaction mixture was stirred for 65 hours at RT. Subsequently, the solvents were evaporated and the residue poured into crashed ice, acidified with HCl (25% in water) and extracted three times with $Et_2O$; the organic phases were dried over magnesium sulfate, filtered and evaporated. The residue was purified by flash column chromatography (heptane/EtOAc 99:1) to give 4.95 g (65%) of the title compound as colorless oil. MS:=325.2 ($MH^+$).

B) 4,6-Dimethyl-2-(3-trifluoromethyl-phenyl)-pyrimidine-5-carboxylic acid

To a solution of 5.21 g (16.1 mmol) of 4,6-dimethyl-2-(3-trifluoromethyl-phenyl)-pyrimidine-5-carboxylic acid ethyl ester in 165 ml of 2-ethoxyethanol/$H_2O$ (9:1) was added 2.62 g=40.2 mmol of potassium hydroxide (86%); then, the reaction mixture was heated up to reflux in an oil bath of 150° C. After 4 hours, it was poured into crashed ice, acidified with HCl (25% in water) and extracted three times with $CH_2Cl_2$; the organic phases were washed with water, dried over magnesium sulfate, filtered and evaporated to give 4.29 g (90%) of the crude title compound as off-white solid. MS: 295.3 ([M−H]$^-$).

Intermediate 6

3-(4,4,5,5-Tetramethyl-[1,3,2]dioxaborolan-2-yl)-5-trifluoromethyl-pyridine

A suspension of 3.50 g (15.50 mmol) of 3-bromo-5-trifluoromethyl-pyridine, 0.54 g (0.8 mmol) of bis(triphenylphosphine)palladium(II) chloride and 4.55 g (46.5 mmol) of potassium acetate in 75 ml of dioxane was stirred for 15 min; then, 6.42 g (24.8 mmol) of 4,4,5,5,4',4',5',5'-octamethyl-[2,2']bi[[1,3,2]dioxaborolanyl](bis-pinacolato-diboron) was added and the mixture was heated up to 100° C. After 20 hours, it was poured into crashed ice, the pH was adjusted to 9-10 with sodium carbonate solution and the mixture then extracted three times with EtOAc; the organic phases were washed with water, dried over magnesium sulfate, filtered and evaporated. The residue was purified by flash column chromatography ($CH_2Cl_2$/MeOH 1:0 to 9:1) to give 3.48 g (82%) of the title compound as a colorless solid. MS: 273.1 ($M^+$).

Intermediate 7

4-Cyclopropyl-6-methyl-2-(3-trifluoromethyl-phenyl)-pyrimidine-5-carboxylic acid A) 4-Cyclopropyl-6-methyl-2-(3-trifluoromethyl-phenyl)-pyrimidine-5-carboxylic acid ethyl ester 2-Cyclopropanecarbonyl-3-oxo-butyric acid ethyl ester [Jung, J.-C.; Watkins, E. B.; Avery, M. A. *Tetrahedron* (2002), 58(18), 3639-3646] (4.7 g, 24 mmol) was dissolved in acetonitrile (40 ml) and cooled to 0° C. Cesium carbonate (7.8 g, 24 mmol) was added and the reaction stirred for 0.5 h before the addition of trifluoro-methanesulfonic acid methyl ester (2.6 ml, 24 mmol) and the reaction stirred for a further 2 h. The reaction mixture was diluted with EtOAc, washed with water, brine, dried (Na$_2$SO$_4$) and concentrated to afford a crude mixture of (E,Z)-2-cyclopropanecarbonyl-3-methoxy-but-2-enoic acid ethyl ester and/or 2-[1-cyclopropyl-1-methoxy-meth-(E,Z)-ylidene]-3-oxo-butyric acid ethyl ester (6.3 g, quant). A third of this material (2.1 g, 8 mmol) was dissolved in ethanol (10 ml) and added dropwise to a solution of 3-trifluoromethyl-benzamidine hydrochloride (1.8 g, 8 mmol) and sodium tert-butoxide (0.8 g, 8 mmol) and the mixture stirred overnight. The reaction was concentrated, re-dissolved in EtOAc, washed with 1N hydrochloric acid solution, dried (Na$_2$SO$_4$) and concentrated. Purification by flash column chromatography (EtOAc/Heptane 1:9) afforded the title product (1.2 g, 42%) as clear oil. MS: 351.2 (MH$^+$).

B) 4-Cyclopropyl-6-methyl-2-(3-trifluoromethyl-phenyl)-pyrimidine-5-carboxylic acid Intermediate 7A (1.2 g, 3 mmol) was dissolved in EtOH and aqueous sodium hydroxide added (1.1 ml, 6M solution in water, 7 mmol) and the reaction heated to reflux for 4 h after which time the reaction was concentrated, re-dissolved in water and the pH adjusted to pH 1 by the addition of 25% hydrochloric acid. The resulting precipitate was isolated by filtration affording the title product (0.7 g, 62%) as a white powder. MS: 321.1 (M−H$^-$).

Intermediate 8

N-((3R,5S)-5-Hydroxymethyl-1-piperidin-4-yl-pyrrolidin-3-yl)-acetamide dihydrochloride A) N-((3R,5S)-5-Hydroxymethyl-pyrrolidin-3-yl)-acetamide hydrochloride A solution of (2S,4R)-4-azido-pyrrolidine-1,2-dicarboxylic acid 1-tert-butyl ester 2-methyl ester [Marusawa, H.; Setoi, H.; Sawada, A.; Kuroda, A.; Seki, J.; Motoyama, Y.; Tanaka, H. *Bioorganic & Medicinal Chemistry* (2002), 10(5), 1399-1415] (1.0 g, 4 mmol) in THF (5 ml) was added to an ice-cooled suspension of LAH (0.6 g, 15 mmol) in THF (5 ml) under Ar. The reaction was stirred for 1 h after which time it was quenched by cautious addition of water. The resulting precipitate was filtered, rinsed with EtOAc and the organics concentrated. The crude (2S,4R)-4-amino-2-hydroxymethyl-pyrrolidine-1-carboxylic acid tert-butyl ester (0.7 g, 3 mmol) thus obtained was then dissolved in CH$_2$Cl$_2$ (15 ml), saturated NaHCO$_3$ (15 ml) was added followed by acetic anhydride (0.3 ml, 3 mmol) and the mixture stirred for 2 h. The reaction mixture was then separated, the organic phase dried (Na$_2$SO$_4$) and concentrated affording crude (2S,4R)-4-acetylamino-2-hydroxymethyl-pyrrolidine-1-carboxylic acid tert-butyl ester (0.62 g, 79%). Treatment of this with a 4 N solution of hydrochloric acid in dioxane afforded the title product (0.5 g, quant) as a yellow powder. MS: 159.1 (MH$^+$).

B) 4-((2S,4R)-4-Acetylamino-2-hydroxymethyl-pyrrolidin-1-yl)-piperidine-1-carboxylic acid tert-butyl ester Intermediate 8A (0.36 g, 2 mmol) was added to a solution of N-tert-butoxycarbony-4-piperidone (0.44 g, 2 mmol), acetic acid (0.25 ml, 4 mmol) and triethylamine (0.60 ml, 2 mmol) in CH$_2$Cl$_2$ (10 ml) and finally sodium triacetoxyborohydride (0.22 g, 3 mmol) was added. The mixture was stirred for 2 h after which time the reaction was washed with saturated NaHCO$_3$, dried (Na$_2$SO$_4$) and concentrated. The residue was purified by flash column chromatography (CH$_2$Cl$_2$/MeOH 9:1) affording the title compound (0.24 g, 32%) as a gum. MS: 342.5 (MH$^+$).

C) N-((3R,5S)-5-Hydroxymethyl-1-piperidin-4-yl-ppyrrolidin-3-yl)-acetamide dihydrochloride Intermediate 8B (0.24 g, 1 mmol) was treated with 4N hydrochloric acid in dioxane (5 ml) for 1 h; concentration afforded the title compound (0.24 g, quant) as a white powder. MS: 242.2 (MH$^+$).

Intermediate 9

((S)-1-Piperidin-4-yl-pyrrolidin-2-yl)-methanol di-hydrochloride

A solution of 3.00 g (10.5 mmol) of 4-((S)-2-hydroxymethyl-pyrrolidin-1-yl)-piperidine-1-carboxylic acid tert-butyl ester (intermediate 3A) in 70 ml of EtOH was treated at RT with 5.27 ml (21.1 mmol) of hydrochloric acid in 1,4-dioxane (4 molar) and the mixture was heated up to 100° C. After two hours, the solvents were evaporated and the residue was re-crystallized from MeOH/MeCN and Et$_2$O to give 2.21 g (82%) of the title compound as colorless solid. MS: 185.2 (MH$^+$).

Intermediate 10

3-Methoxy-5-methyl-3'-trifluoromethyl-biphenyl-4-carboxylic acid

A) 3-Methoxy-5-methyl-3'-trifluoromethyl-biphenyl-4-ylamine

In analogy to the procedure described in example 1, 4-bromo-2-methoxy-6-methyl-phenylamine [Chan, J. H.; Hong, J. S.; Hunter, R. N., III; Orr, G. F.; Cowan, J. R.; Sherman, D. B.; Sparks, St. M.; Reitter, B. E.; Andrews, C. W., III; Hazen, R. J.; St. Clair, M.; Boone, L. R.; Ferris, R. G.; Creech, K. L.; Roberts, G. B.; Short, St. A.; Weaver, K.; Ott, R. J.; Ren, J.; Hopkins, A.; Stuart, D. I.; Stammers, D. K. *Journal of Medicinal Chemistry* (2001), 44(12), 1866-1882] was reacted with 3-trifluoromethyl-phenyl boronic acid in DMF at 80° C. in the presence of potassium phosphate solution and tetrakis-(triphenylphosphine)-palladium to give the title compound as brown oil. MS: 282.1 (MH$^+$).

B) 4-Iodo-3-methoxy-5-methyl-3'-trifluoromethyl-biphenyl

A solution of 3.10 g (45.0 mmol) of sodium nitrite in 20 ml of H$_2$O was added to a suspension of 11.50 g (40.90 mmol) of 3-methoxy-5-methyl-3'-trifluoromethyl-biphenyl-4-ylamine in 35.0 ml of HCl (25%) and 190 ml of H$_2$O at 2° C.; after 30 min, the light-brown solution formed was added at 0° C. to a solution of 6.95 g (433.4 mmol) of potassium iodide in 40 ml of H$_2$O and the reaction mixture was warmed up to RT. 4 hours later, it was poured then into crashed ice and extracted twice with EtOAc; the organic phases were washed with sodium bicarbonate solution and with water, dried over magnesium sulfate, filtered and evaporated. The residue was purified by flash column chromatography (heptane/EtOAc 1:0 to 4:1) to give 7.79 g (49%) of the title compound as yellow oil. MS: 392.0 (M$^+$).

C) 3-Methoxy-5-methyl-3'-trifluoromethyl-biphenyl-4-carboxylic acid

A solution of 7.70 g (19.6 mmol) of 4-iodo-3-methoxy-5-methyl-3'-trifluoromethyl-biphenyl in 190 ml of THF was cooled down to −75° C.; then, 13.5 ml (21.6 mmol) of an n-butyl lithium solution (1.6 molar in n-hexane) was added slowly below −70° C. One hour later, the dark-brown reaction mixture was treated with an excess of carbon dioxide gas (dried by bubbling through $H_2SO_4$ conc. in a gas washing device) during 2 hours and then warmed up to 0° C. It was subsequently poured into crashed ice, the pH was then adjusted to 3-4 with $HCl/H_2O$ (1N) and the mixture was extracted twice with EtOAc; the organic phases were washed with water, dried over magnesium sulfate, filtered and evaporated. The residue was purified by re-crystallization from EtOAc/heptane to give 2.90 g (48%) of the title compound as colorless solid. MS: 309.3 (M−H$^-$).

Intermediate 11

5-Methyl-3-pyrimidin-5-yl-3'-trifluoromethyl-biphenyl-4-carboxylic acid

A) 3-Hydroxy-5-methyl-3'-trifluoromethyl-biphenyl-4-carboxylic acid

A suspension of 4.05 g (13.1 mmol) of 3-methoxy-5-methyl-3'-trifluoromethyl-biphenyl-4-carboxylic acid (intermediate 10 C) in 130 ml of $CH_2Cl_2$ was cooled down to 2° C. and then 26.1 ml (26.1 mmol) of a solution of boron tribromide (1 molar in $CH_2Cl_2$) was added below 5° C. The color of the reaction mixture changed from light to dark yellow. After stirring at RT for 2 hours, the reaction mixture was poured into crashed ice and extracted twice with $CH_2Cl_2$; the organic phases were washed with water, dried over magnesium sulfate, filtered and evaporated. The residue was purified by re-crystallization from EtOAc/heptane to give 3.70 g (96%) of the title compound as off-white solid. MS: 295.1 (M−H$^-$).

B) 3-Hydroxy-5-methyl-3'-trifluoromethyl-biphenyl-4-carboxylic acid methyl ester A solution of 2.20 g (7.40 mmol) of 3-hydroxy-5-methyl-3'-trifluoromethyl-biphenyl-4-carboxylic acid in 70 ml of MeOH was treated at RT with 0.84 ml=1.53 g (14.9 mmol) of sulfuric acid (95%) and 0.5 g of molecular sieves (0.4 nm) and the reaction mixture was heated at reflux for 72 hours. It was then cooled down to RT, filtered and the residue was washed with MeOH. The filtrate was evaporated and this residue was dissolved in $CH_2Cl_2$ and poured into crashed ice and extracted twice with $CH_2Cl_2$; the organic phases were washed with water, dried over magnesium sulfate, filtered and evaporated. The residue was purified by flash column chromatography (heptane/EtOAc 4:1) to give 1.04 g (45%) of the title compound as colorless solid. MS: 310.0 (M$^+$).

C) 5-Methyl-3-trifluoromethanesulfonyloxy-3'-trifluoromethyl-biphenyl-4-carboxylic acid methyl ester 1.12 ml=0.848 g (6.40 mmol) of N-ethyldiisopropylamine was added to a solution of 1.33 g (4.30 mmol) of 3-hydroxy-5-methyl-3'-trifluoromethyl-biphenyl-4-carboxylic acid methyl ester in 25 ml of $CH_2Cl_2$ at RT and the reaction mixture was then cooled down to −50° C. 1.08 ml=1.851 g (6.40 mmol) of trifluoromethanesulfonic anhydride was added drop by drop and the reaction mixture was then warmed up to 0° C. It was subsequently poured into crashed ice and extracted twice with $CH_2Cl_2$; the organic phases were washed with water, dried over magnesium sulfate, filtered and evaporated. The residue was purified by flash column chromatography (heptane/EtOAc 1:0 to 19:1) to give 1.70 g (90%) of the title compound as colorless oil. MS: 442.0 (M$^+$).

D) 5-Methyl-3-pyrimidin-5-yl-3'-trifluoromethyl-biphenyl-4-carboxylic acid methyl ester In analogy to the procedure described in example 1,5-methyl-3-trifluoromethanesulfonyloxy-3'-trifluoromethyl-biphenyl-4-carboxylic acid methyl ester was reacted with pyrimidine-5-yl-boronic acid in DMF at 80° C. in the presence of potassium phosphate solution and tetrakis-(triphenylphosphine)-palladium to give the title compound as colorless oil. MS: 372.0 (M$^+$).

E) 5-Methyl-3-pyrimidin-5-yl-3'-trifluoromethyl-biphenyl-4-carboxylic acid

To a solution of 0.43 g (1.20 mmol) of 5-methyl-3-pyrimidin-5-yl-3'-trifluoromethyl-biphenyl-4-carboxylic acid methyl ester in 12 ml of THF/MeOH (1:1) was added 2.89 ml (2.90 mmol) of lithium hydroxide solution (1 molar in water) drop by drop and the reaction mixture was then heated up to 50° C. After 40 hours, the reaction mixture was poured into crashed ice and acidified with $HCl/H_2O$ (1N) to pH 3.0 and then extracted twice with EtOAc; the organic phases were washed with water, dried over magnesium sulfate, filtered and evaporated. The residue was purified by flash column chromatography ($CH_2Cl_2$/MeOH 1:0 to 3:2) to give 0.410 g (99%) of the title compound as colorless solid. MS: 357.0 (M−H$^-$).

Intermediate 12

2-Methoxy-4-methyl-6-(3-trifluoromethyl-phenyl)-nicotinic acid

A) 2,6-Dichloro-4-methyl-nicotinic acid methyl ester

To a solution of 8.05 g (39.1 mmol) of 2,6-dichloro-4-methyl-nicotinic acid [Lamm, G. *Ger. Offen.* (1977), DE 2538950] in 100 ml of DMF was added 8.10 g (58.6 mmol) of potassium carbonate. While stirring, 12.16 ml=27.7 g (195.4 mmol) of iodomethane was added drop by drop and the reaction mixture was stirred for 6 hours at RT. It was then poured into crashed ice and extracted twice with EtOAc; the organic phases were washed with water, dried over magnesium sulfate, filtered and evaporated to give 8.47 g (99%) of the title compound as light yellow solid. MS: 219.0 (M$^+$, 2Cl).

B) 6-Chloro-2-methoxy-4-methyl-nicotinic acid methyl ester

To a solution of 6.50 g (29.5 mmol) of 2,6-dichloro-4-methyl-nicotinic acid methyl ester in 75 ml of $CH_2Cl_2$ was added at 0° C. 6.56 ml (35.4 mmol) of a sodium methoxide solution (5.4 molar in MeOH). After 16 hours, the reaction mixture was warmed up to RT and stirred again 16 hours at this temperature and subsequently poured into crashed ice; then, the pH was adjusted to 4-5 with 2N acetic acid and the reaction mixture was extracted twice with $CH_2Cl_2$; the organic phases were washed with water, dried over magnesium sulfate, filtered and evaporated. The residue was purified by flash column chromatography (heptane/EtOAc 1.0 to 98:2) to give 5.79 g (91%) of the title compound as colorless solid. MS: 216.1 (MH+, 1Cl).

C) 2-Methoxy-4-methyl-6-(3-trifluoromethyl-phenyl)-nicotinic acid methyl ester To a solution of 5.75 g (26.7 mmol) of 6-chloro-2-methoxy-4-methyl-nicotinic acid methyl ester in 250 ml of DMF was added 10.13 g (53.3 mmol) of 3-trifluoromethyl-phenylboronic acid followed by 50.0 ml of a solution of tribasic potassium phosphate (2 M in water). Finally, 1.54 g (1.3 mmol) of tetrakis-(triphenylphosphine)-palladium was added and the reaction mixture was subsequently warmed up to 80° C. After 5 hours, it was cooled down to RT, poured into crashed ice and extracted twice with CH$_2$Cl$_2$; the organic phases were washed with water, dried over magnesium sulfate, filtered and evaporated. The residue was purified by flash column chromatography (heptane/EtOAc 1:0 to 9:1) to give 8.54 g (98%) of the title compound as light yellow oil. MS: 326.1 (MH+).

D) 2-Methoxy-4-methyl-6-(3-trifluoromethyl-phenyl)-nicotinic acid

To a solution of 0.325 g (1.00 mmol) of 2-methoxy-4-methyl-6-(3-trifluoromethyl-phenyl)-nicotinic acid methyl ester in 20 ml of THF/MeOH (1:1) was added 2.50 ml (2.50 mmol) of lithium hydroxide solution (1 molar in water) drop by drop and the reaction mixture was then heated up to reflux. After 8 hours, it was poured into crashed ice and acidified with HCl/H$_2$O (1N) to pH 3.0 and then extracted twice with EtOAc; the organic phases were washed with water, dried over magnesium sulfate, filtered and evaporated. The residue was purified by flash column chromatography (CH$_2$Cl$_2$/MeOH 1:0 to 4:1) to give 0.24 g (77%) of the title compound as light yellow solid. MS: 310.0 (M−H−).

Intermediate 13

2-(2-Benzyloxy-ethoxy)-4-methyl-6-(3-trifluoromethyl-phenyl)-nicotinic acid

A) 4-Methyl-2-oxo-6-(3-trifluoromethyl-phenyl)-1,2-dihydro-pyridine-3-carboxylic acid A solution of 0.325 g (1.0 mmol) of 2-methoxy-4-methyl-6-(3-trifluoromethyl-phenyl)-nicotinic acid methyl ester (intermediate 12C) in 10 ml of CH$_2$Cl$_2$ was cooled down to 0° C., 2.0 ml (2.0 mmol) of a solution of boron tribromide (1 molar in CH$_2$Cl$_2$) was added drop by drop and the reaction mixture was subsequently warmed up to RT. After two hours, 1.0 ml of MeOH was added and 90 min later, the reaction mixture was evaporated. The crude intermediate formed was used without purification in the next step.

B) 4-Methyl-2-oxo-6-(3-trifluoromethyl-phenyl)-1,2-dihydro-pyridine-3-carboxylic acid methyl ester A solution of 0.30 g (1.0 mmol) of 4-methyl-2-oxo-6-(3-trifluoromethyl-phenyl)-1,2-dihydro-pyridine-3-carboxylic acid in 15 ml of MeOH was treated with 0.06 ml=0.01 g (0.1 mmol) of H$_2$SO$_4$ (98%) and the reaction mixture was heated up to reflux. After 4 hours, it was cooled down to RT, poured into crashed ice and extracted twice with CH$_2$Cl$_2$; the organic phases were washed with water, dried over magnesium sulfate, filtered and evaporated. The residue was purified by flash column chromatography (CH$_2$Cl$_2$/MeOH 1:0 to 9:1) to give 0.24 g (77%) of the title compound as off-white solid. MS: 312.0 (MH+).

C) 2-(2-Benzyloxy-ethoxy)-4-methyl-6-(3-trifluoromethyl-phenyl)-nicotinic acid methyl ester A solution of 0.62 g (2.0 mmol) of 4-methyl-2-oxo-6-(3-trifluoromethyl-phenyl)-1,2-dihydro-pyridine-3-carboxylic acid methyl ester in 10 ml of DMSO was treated at RT with 1.947 g (6.0 mmol) of cesium carbonate and 0.066 g (0.4 mmol) of potassium iodide. 0.38 ml=0.514 g (2.4 mmol) of (2-bromo-ethoxymethyl)-benzene was added drop by drop and the reaction mixture was stirred for 16 hours at RT. It was then poured into crashed ice and extracted three times with CH$_2$Cl$_2$; the organic phases were washed with water, dried over magnesium sulfate, filtered and evaporated. The residue was purified by flash column chromatography (heptane/EtOAc 1:0 to 1:1) to give 0.73 g (82%) of the title compound as light yellow oil. MS: 446.2 (MH+).

C) 2-(2-Benzyloxy-ethoxy)-4-methyl-6-(3-trifluoromethyl-phenyl)-nicotinic acid In analogy to the procedure described for the preparation of intermediate 4B, 2-(2-benzyloxy-ethoxy)-4-methyl-6-(3-trifluoromethyl-phenyl)-nicotinic acid methyl ester was saponified to give the title compound as colorless solid. MS: 430.2 (M−H−).

Example 1

(3,5-Dimethyl-3'-trifluoromethoxy-biphenyl-4-yl)-(4-pyrrolidin-1-yl-piperidin-1-yl)-methanone

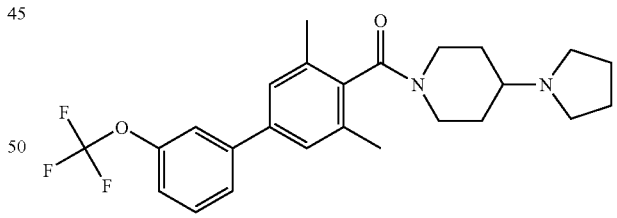

To a degassed solution of 0.130 g (0.35 mmol) of (4-bromo-2,6-dimethyl-phenyl)-(4-pyrrolidin-1-yl-piperidin-1-yl)-methanone (intermediate 1) and 0.147 g (0.70 mmol) of 3-trifluoromethoxy-phenyl boronic acid in 5 ml of DMF was added 2.50 ml of tribasic potassium phosphate solution (2M in water) drop by drop, followed by 0.022 g (0.019 mmol) of tetrakis-(triphenylphosphine)-palladium. This reaction mixture was stirred at 80° C. for two hours and subsequently cooled down to RT, then poured into crashed ice and extracted three times with CH$_2$Cl$_2$; the organic phases were washed with water, dried over magnesium sulfate, filtered and evaporated. The residue was purified by flash column chromatography (CH₂Cl₂/MeOH 1:0 to 95:5) to give 0.12 g (77%) of the title compound as light yellow amorphous solid. MS: 447.2 (MH⁺).

Example 2

(3,5-Dimethyl-3'-trifluoromethyl-biphenyl-4-yl)-(4-pyrrolidin-1-yl-piperidin-1-yl)-methanone

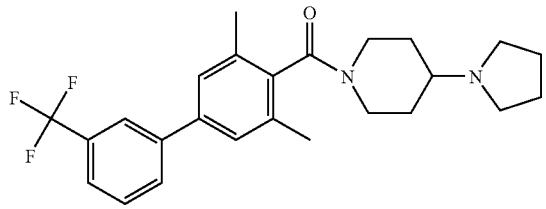

In analogy to the procedure described for example 1, (4-bromo-2,6-dimethyl-phenyl)-(4-pyrrolidin-1-yl-piperidin-1-yl)-methanone (intermediate 1) was reacted with 3-trifluoromethyl-phenyl boronic acid to give the title compound as off-white amorphous solid. MS: 431.4 (MH⁺).

Example 3

(3,5-Dimethyl-3'-trifluoromethoxy-biphenyl-4-yl)-[4-(2-hydroxy-ethyl)-[1,4]diazepan-1-yl]-methanone

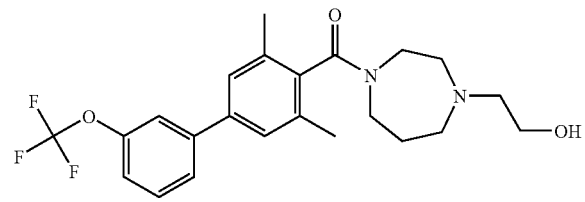

In analogy to the procedure described for example 1, (4-bromo-2,6-dimethyl-phenyl)-[4-(2-hydroxy-ethyl)-[1,4] diazepan-1-yl]-methanone (prepared from 4-bromo-2,6-dimethyl-benzoic acid and 2-[1,4]diazepan-1-yl-ethanol in analogy to the procedure described for the preparation of intermediate 1) was reacted with 3-trifluoromethoxy-phenyl boronic acid to give the title compound as light yellow amorphous solid. MS: 437.3 (MH⁺).

Example 4

(2-Methyl-3'-trifluoromethoxy-biphenyl-3-yl)-(4-pyrrolidin-1-yl-piperidin-1-yl)-methanone

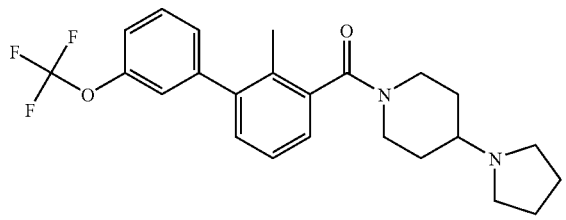

In analogy to the procedure described for example 1, (3-bromo-2-methyl-phenyl)-(4-pyrrolidin-1-yl-piperidin-1-yl)-methanone (intermediate 2) was reacted with 3-trifluoromethoxy-phenyl boronic acid to give the title compound as dark brown amorphous solid. MS: 433.3 (MH⁺).

Example 5

(2-Methyl-3'-trifluoromethyl-biphenyl-3-yl)-(4-pyrrolidin-1-yl-piperidin-1-yl)-methanone

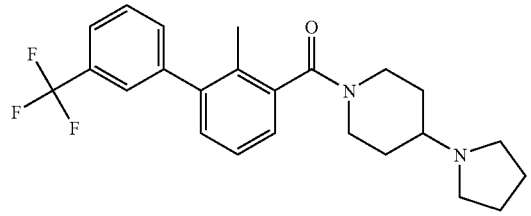

In analogy to the procedure described for example 1, (3-bromo-2-methyl-phenyl)-(4-pyrrolidin-1-yl-piperidin-1-yl)-methanone (intermediate 2) was reacted with 3-trifluoromethyl-phenyl boronic acid to give the title compound as dark brown amorphous solid. MS: 417.3 (MH⁺).

Example 6

(3-Methyl-3'-trifluoromethoxy-biphenyl-4-yl)-(4-pyrrolidin-1-yl-piperidin-1-yl)-methanone

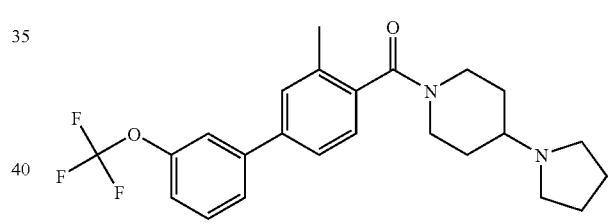

In analogy to the procedure described for example 1, (4-bromo-2-methyl-phenyl)-(4-pyrrolidin-1-yl-piperidin-1-yl)-methanone (prepared from 4-bromo-2-methyl-benzoic acid and 4-pyrrolidin-1-yl-piperidine in analogy to the procedure described for the preparation of intermediate 2) was reacted with 3-trifluoromethoxy-phenyl boronic acid to give the title compound as light yellow solid. MS: 433.3 (MH⁺).

Example 7

(3-Methyl-3'-trifluoromethyl-biphenyl-4-yl)-(4-pyrrolidin-1-yl-piperidin-1-yl)-methanone

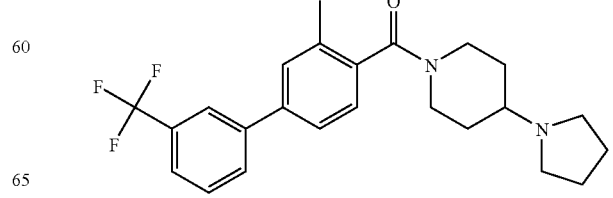

In analogy to the procedure described for example 1, (4-bromo-2-methyl-phenyl)-(4-pyrrolidin-1-yl-piperidin-1-yl)-methanone (prepared from 4-bromo-2-methyl-benzoic acid and 4-pyrrolidin-1-yl-piperidine in analogy to the procedure described for the preparation of intermediate 2) was reacted with 3-trifluoromethyl-phenyl boronic acid to give the title compound as off-white amorphous solid. MS: 417.4 (MH+).

Example 8

(2,4-Dimethyl-3'-trifluoromethoxy-biphenyl-3-yl)-(4-pyrrolidin-1-yl-piperidin-1-yl)-methanone

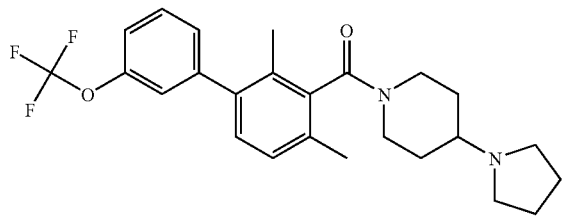

In analogy to the procedure described for intermediate 1, 2,4-dimethyl-3'-trifluoromethoxy-biphenyl-3-carboxylic acid (prepared from 3-bromo-2,6-dimethyl-benzoic acid [Lee, J.; et al. *Bioorganic & Medicinal Chemistry Letters* (2003), 13(11), 1879-1882] and 3-trifluoromethoxy-phenyl boronic acid in analogy to the procedure described for the preparation of example 1) was converted into its acid chloride and reacted with 4-pyrrolidin-1-yl-piperidine to give the title compound as light yellow solid. MS: 447.3 (MH+).

Example 9

(3,5-Dimethyl-3'-trifluoromethyl-biphenyl-4-yl)-[4-((S)-2-hydroxymethyl-pyrrolidin-1-yl)-piperidin-1-yl]-methanone

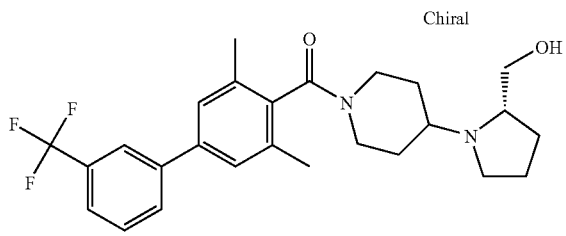

In analogy to the procedure described for example 1, (4-bromo-2,6-dimethyl-phenyl)-[4-((S)-2-hydroxymethyl-pyrrolidin-1-yl)-piperidin-1-yl]-methanone (intermediate 4) was reacted with 3-trifluoromethyl-phenyl boronic acid to give the title compound as colorless amorphous solid. MS: 461.3 (MH+).

Example 10

(3,5-Dimethyl-3'-trifluoromethoxy-biphenyl-4-yl)-[4-((S)-2-hydroxymethyl-pyrrolidin-1-yl)-piperidin-1-yl]-methanone

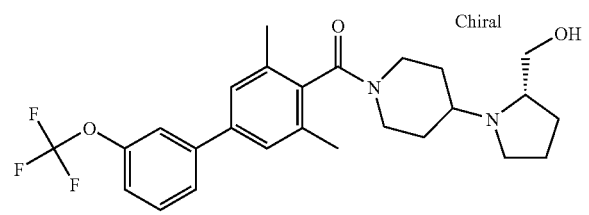

In analogy to the procedure described for example 1, (4-bromo-2,6-dimethyl-phenyl)-[4-((S)-2-hydroxymethyl-pyrrolidin-1-yl)-piperidin-1-yl]-methanone (intermediate 4) was reacted with 3-trifluoromethoxy-phenyl boronic acid to give the title compound as off-white solid. MS: 477.2 (MH+).

Example 11

(3,5-Dimethyl-4'-trifluoromethyl-biphenyl-4-yl)-[4-((S)-2-hydroxymethyl-pyrrolidin-1-yl)-piperidin-1-yl]-methanone

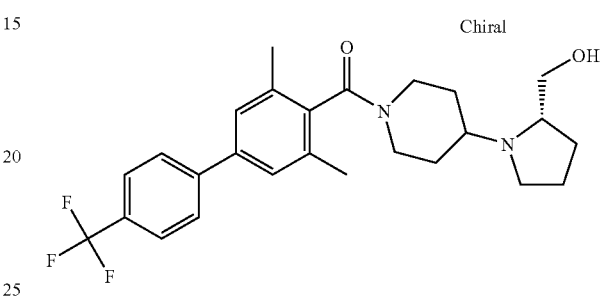

In analogy to the procedure described for example 1, (4-bromo-2,6-dimethyl-phenyl)-[4-((S)-2-hydroxymethyl-pyrrolidin-1-yl)-piperidin-1-yl]-methanone (intermediate 4) was reacted with 4-trifluoromethyl-phenyl boronic acid to give the title compound as off-white solid. MS: 461.3 (MH+).

Example 12

(3,5-Dimethyl-3',5'-bis-trifluoromethyl-biphenyl-4-yl)-[4-((S)-2-hydroxymethyl-pyrrolidin-1-yl)-piperidin-1-yl]-methanone

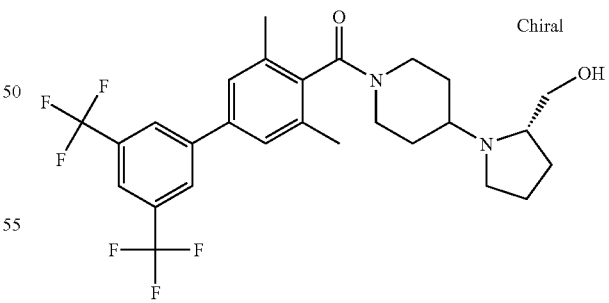

In analogy to the procedure described for example 1, (4-bromo-2,6-dimethyl-phenyl)-[4-((S)-2-hydroxymethyl-pyrrolidin-1-yl)-piperidin-1-yl]-methanone (intermediate 4) was reacted with 3,5-bis-trifluoromethyl-phenyl boronic acid to give the title compound as colorless solid. MS: 529.2 (MH+).

Example 13

[4,6-Dimethyl-2-(3-trifluoromethyl-phenyl)-pyrimidin-5-yl]-(4-pyrrolidin-1-yl-piperidin-1-yl)-methanone

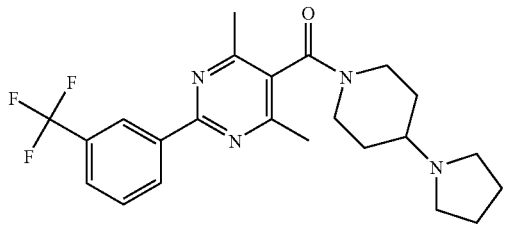

In analogy to the procedure described for intermediate 1,4,6-dimethyl-2-(3-trifluoromethyl-phenyl)-pyrimidine-5-carboxylic acid (intermediate 5) was converted into its acid chloride and reacted with 4-pyrrolidin-1-yl-piperidine to give the title compound as off-white solid. MS: 433.3 (MH$^+$).

Example 14

[2,6-Dimethyl-4-(5-trifluoromethyl-pyridin-3-yl)-phenyl]-[4-((S)-2-hydroxymethyl-pyrrolidin-1-yl)-piperidin-1-yl]-methanone

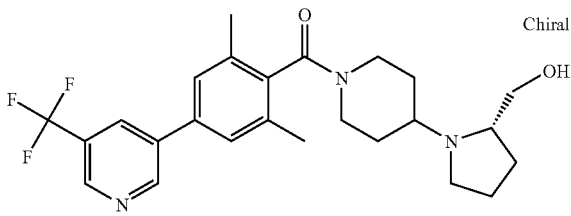

In analogy to the procedure described for example 1, (4-bromo-2,6-dimethyl-phenyl)-[4-((S)-2-hydroxymethyl-pyrrolidin-1-yl)-piperidin-1-yl]-methanone (intermediate 4) was reacted with 3-(4,4,5,5-tetramethyl-[1,3,2]dioxaborolan-2-yl)-5-trifluoromethyl-pyridine (intermediate 6) to give the title compound as light yellow solid. MS: 462.4 (MH$^+$).

Example 15

[2-(3,5-Bis-trifluoromethyl-phenyl)-4,6-dimethyl-pyrimidin-5-yl]-(4-pyrrolidin-1-yl-piperidin-1-yl)-methanone

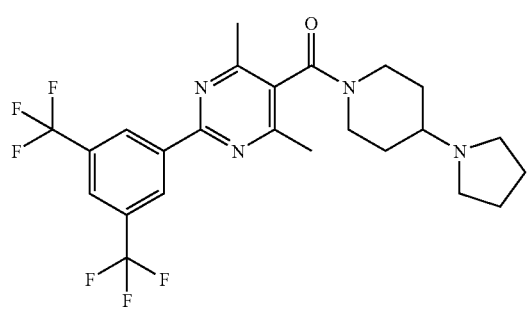

In analogy to the procedure described for intermediate 1,2-(3,5-bis-trifluoromethyl-phenyl)-4,6-dimethyl-pyrimidine-5-carboxylic acid [prepared by reaction of 3,5-bis-trifluoromethyl-benzamidine hydrochloride with (E,Z)-2-acetyl-3-methoxy-but-2-enoic acid ethyl ester to give 2-(3,5-bis-trifluoromethyl-phenyl)-4,6-dimethyl-pyrimidine-5-carboxylic acid ethyl ester followed by saponification in analogy to the procedures described for the preparation of intermediate 5] was converted into its acid chloride and reacted with 4-pyrrolidin-1-yl-piperidine to give the title compound as colorless solid. MS: 501.1 (MH$^+$).

Example 16

[4,6-Dimethyl-2-(3-trifluoromethyl-phenyl)-pyrimidin-5-yl]-[4-((S)-2-hydroxymethyl-pyrrolidin-1-yl)-piperidin-1-yl]-methanone

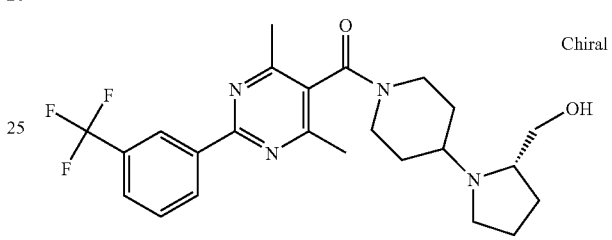

In analogy to the procedures described for intermediate 1 and for intermediate 4 B), 4,6-dimethyl-2-(3-trifluoromethyl-phenyl)-pyrimidine-5-carboxylic acid (intermediate 5) was converted into its acid chloride and subsequently reacted with benzoic acid (S)-1-piperidin-4-yl-pyrrolidin-2-ylmethyl ester (intermediate 3) to give benzoic acid (S)-1-{1-[4,6-dimethyl-2-(3-trifluoromethyl-phenyl)-pyrimidine-5-carbonyl]-piperidin-4-yl}-pyrrolidin-2-ylmethyl ester, which was subsequently saponified to give the title compound as colorless solid. MS: 463.2 (MH$^+$).

Example 17

[2-(3,5-Bis-trifluoromethyl-phenyl)-4,6-dimethyl-pyrimidin-5-yl]-[4-((S)-2-hydroxymethyl-pyrrolidin-1-yl)-piperidin-1-yl]-methanone

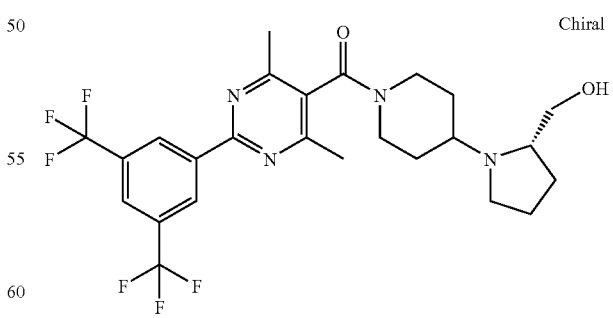

In analogy to the procedures described for intermediate 1 and for intermediate 4 B), 2-(3,5-bis-trifluoromethyl-phenyl)-4,6-dimethyl-pyrimidine-5-carboxylic acid (example 15) was converted into its acid chloride and subsequently reacted with benzoic acid (S)-1-piperidin-4-yl-pyrrolidin-2- ylmethyl ester (intermediate 3) to give benzoic acid (S)-1-{1-[2-(3,5-bis-trifluoromethyl-phenyl)-4,6-dimethyl-pyrimidine-5-carbonyl]-piperidin-4-yl}-pyrrolidin-2-ylmethyl ester, which was subsequently saponified to give the title compound as colorless solid. MS: 531.2 (MH$^+$).

Example 18

[4-Cyclopropyl-6-methyl-2-(3-trifluoromethyl-phenyl)-pyrimidin-5-yl]-(4-pyrrolidin-1-yl-piperidin-1-yl)-methanone

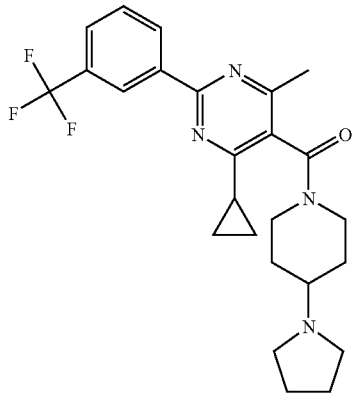

In analogy to the procedure described for intermediate 2, 4-cyclopropyl-6-methyl-2-(3-trifluoromethyl-phenyl)-pyrimidine-5-carboxylic acid (intermediate 7) was reacted with HATU, triethylamine and 4-pyrrolidin-1-yl-piperidine in DMF. Subsequent purification by preparative HPLC afforded the title compound as a gum. MS: 459.5 (MH$^+$).

Example 19

[4-Cyclopropyl-6-methyl-2-(3-trifluoromethyl-phenyl)-pyrimidin-5-yl]-[4-((S)-2-hydroxymethyl-pyrrolidin-1-yl)-piperidin-1-yl]-methanone

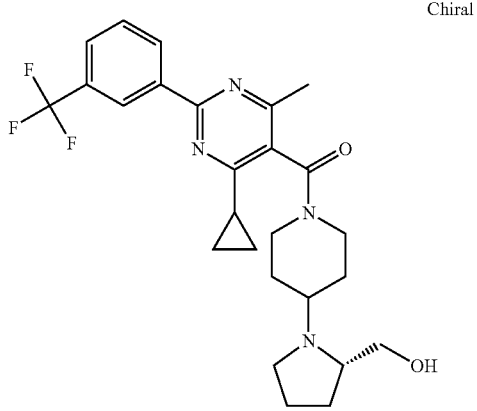

In analogy to the procedure described for intermediate 2, 4-cyclopropyl-6-methyl-2-(3-trifluoromethyl-phenyl)-pyrimidine-5-carboxylic acid (intermediate 7) was reacted with HATU, triethylamine and ((S)-1-piperidin-4-yl-pyrrolidin-2-yl)-methanol di-hydrochloride (intermediate 9) in DMF. Subsequent purification by preparative HPLC afforded the title compound as a gum. MS: 489.6 (MH$^+$).

Example 20

N-((3R,5S)-1-{1-[4-Cyclopropyl-6-methyl-2-(3-trifluoromethyl-phenyl)-pyrimidine-5-carbonyl]-piperidin-4-yl}-5-hydroxymethyl-pyrrolidin-3-yl)-acetamide

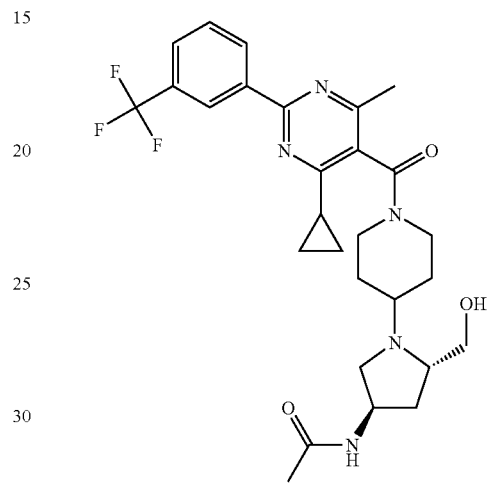

In analogy to the procedure described for intermediate 2, 4-cyclopropyl-6-methyl-2-(3-trifluoromethyl-phenyl)-pyrimidine-5-carboxylic acid (intermediate 7) was reacted with HATU, triethylamine and N-((3R,5S)-5-hydroxymethyl-1-piperidin-4-yl-pyrrolidin-3-yl)-acetamide dihydrochloride (intermediate 8) in DMF. Subsequent purification by preparative HPLC afforded the title compound as a gum. MS: 546.6 (MH$^+$).

Example 21

(3,5-Dimethyl-4'-trifluoromethoxy-biphenyl-4-yl)-[4-((S)-2-hydroxymethyl-pyrrolidin-1-yl)-piperidin-1-yl]-methanone

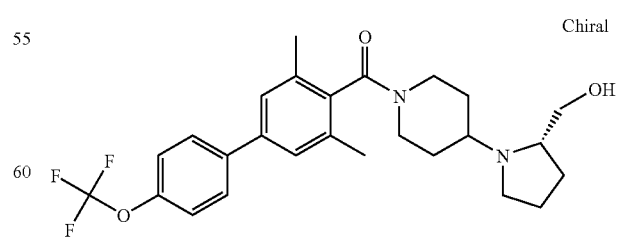

In analogy to the procedure described for example 1, (4-bromo-2,6-dimethyl-phenyl)-[4-((S)-2-hydroxymethyl-pyrrolidin-1-yl)-piperidin-1-yl]-methanone (intermediate 4)

was reacted with 4-trifluoromethoxy-phenyl boronic acid to give the title compound as light yellow solid. MS: 477.1 (MH⁺).

Example 22

(3,5-Dimethyl-3'-trifluoromethyl-biphenyl-4-yl)-(4-hydroxy-[1,4']bipiperidinyl-1'-yl)-methanone

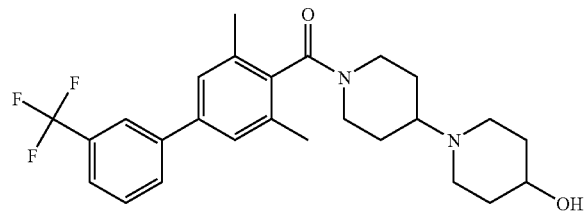

In analogy to the procedures described for intermediates 3B, 3C, 1, 4B and for example 1, the title compound has been prepared by the following reaction sequence: i) 4-hydroxy-[1,4']bipiperidinyl-1'-carboxylic acid tert-butyl ester [Lawrence, L.; Rigby, A.; Sanganee, H.; Springthorpe, B. *PCT Int. Appl.* (2001), WO 2001077101 A1] was reacted with benzoyl chloride to give 4-benzoyloxy-[1,4']bipiperidinyl-1'-carboxylic acid tert-butyl ester; ii) 4-benzoyloxy-[1,4']bipiperidinyl-1'-carboxylic acid tert-butyl ester was reacted with trifluoroacetic acid to give benzoic acid [1,4']bipiperidinyl-4-yl ester; iii) 4-bromo-2,6-dimethyl-benzoic acid was converted into its acid chloride and reacted with benzoic acid [1,4']bipiperidinyl-4-yl ester to give benzoic acid 1'-(4-bromo-2,6-dimethyl-benzoyl)-[1,4']bipiperidinyl-4-yl ester; iv) benzoic acid 1'-(4-bromo-2,6-dimethyl-benzoyl)-[1,4']bipiperidinyl-4-yl ester was saponified to give (4-bromo-2,6-dimethyl-phenyl)-(4-hydroxy-[1,4']bipiperidinyl-1'-yl)-methanone; v) Suzuki reaction of (4-bromo-2,6-dimethyl-phenyl)-(4-hydroxy-[1,4']bipiperidinyl-1'-yl)-methanone with 3-trifluoromethyl-phenyl boronic acid gave the title compound as light brown solid. MS: 461.3 (MH⁺).

Example 23

(3,5-Dimethyl-4'-trifluoromethoxy-biphenyl-4-yl)-(4-hydroxy-[1,4']bipiperidinyl-1'-yl)-methanone

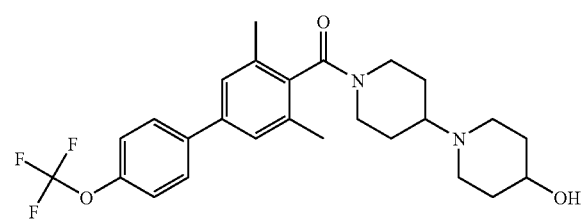

In analogy to the procedure described for example 1, (4-bromo-2,6-dimethyl-phenyl)-(4-hydroxy-[1,4']bipiperidinyl-1'-yl)-methanone (example 22) was reacted with 4-trifluoromethoxy-phenyl boronic acid to give the title compound as light yellow solid. MS: 477.2 (MH⁺).

Example 24

[2,6-Dimethyl-4-(5-trifluoromethyl-pyridin-3-yl)-phenyl]-(4-hydroxy-[1,4']bipiperidinyl-1'-yl)-methanone

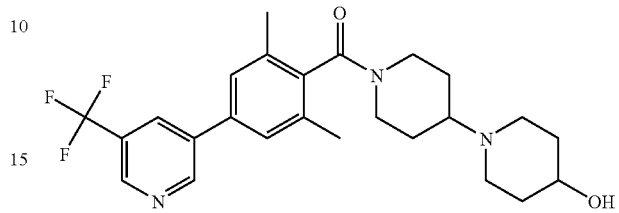

In analogy to the procedure described for example 1, (4-bromo-2,6-dimethyl-phenyl)-(4-hydroxy-[1,4']bipiperidinyl-1'-yl)-methanone (example 22) was reacted with 3-(4,4,5,5-tetramethyl-[1,3,2]dioxaborolan-2-yl)-5-trifluoromethyl-pyridine (intermediate 6) to give the title compound as light yellow oil. MS: 462.2 (MH⁺).

Example 25

[4,6-Dimethyl-2-(3-trifluoromethyl-phenyl)-pyrimidin-5-yl]-(4-hydroxy-[1,4']bipiperidinyl-1'-yl)-methanone

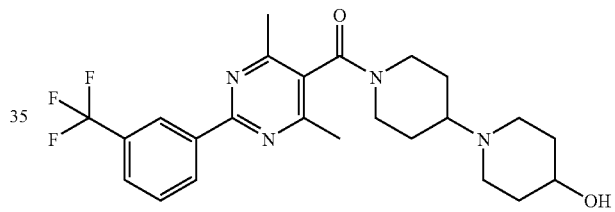

In analogy to the procedures described for intermediate 1 and for intermediate 4 B, 4,6-dimethyl-2-(3-trifluoromethyl-phenyl)-pyrimidine-5-carboxylic acid (intermediate 5) was converted into its acid chloride, reacted with benzoic acid [1,4']bipiperidinyl-4-yl ester (example 22) and subsequently saponified to give the title compound as colorless solid. MS: 463.3 (MH⁺).

Example 26

[2-(3,5-Bis-trifluoromethyl-phenyl)-4,6-dimethyl-pyrimidin-5-yl]-(4-hydroxy-[1,4']bipiperidinyl-1'-yl)-methanone

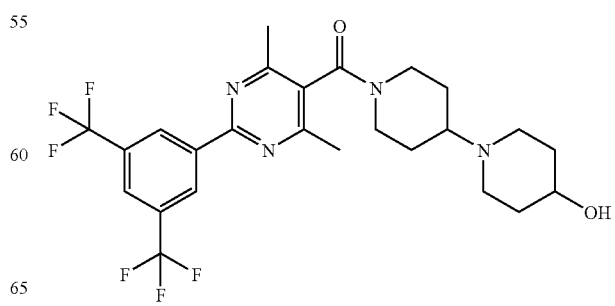

In analogy to the procedures described for intermediate 1 and for intermediate 4 B, 2-(3,5-bis-trifluoromethyl-phenyl)-4,6-dimethyl-pyrimidine-5-carboxylic acid (example 15) was converted into its acid chloride, reacted with benzoic acid [1,4']bipiperidinyl-4-yl ester (example 22) and subsequently saponified to give the title compound as colorless solid. MS: 531.1 (MH+).

Example 27

[2,4-Dimethyl-6-(3-trifluoromethyl-phenyl)-pyridin-3-yl]-(4-pyrrolidin-1-yl-piperidin-1-yl)-methanone

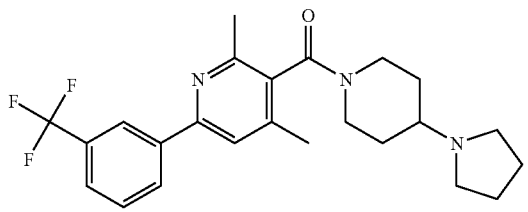

In analogy to the procedures described for example 1, for intermediate 5B and for intermediate 1, the title compound has been prepared by the following reaction sequence: i) 6-chloro-2,4-dimethyl-nicotinic acid ethyl ester [Zhou, Y.; Bridger, G. J.; Skerlj, R. T.; Bogucki, D.; Yang, W.; Bourque, E.; Langille, J.; Li, T.-S.; Metz, M. U.S. Pat. Appl. Publ. (2005), US 2005277668 A1] was reacted with 3-trifluoromethyl-phenyl boronic acid to give 2,4-dimethyl-6-(3-trifluoromethyl-phenyl)-nicotinic acid ethyl ester; ii) 2,4-dimethyl-6-(3-trifluoromethyl-phenyl)-nicotinic acid ethyl ester has been saponified to give 2,4-dimethyl-6-(3-trifluoromethyl-phenyl)-nicotinic acid; iii) 2,4-dimethyl-6-(3-trifluoromethyl-phenyl)-nicotinic acid was converted into its acid chloride and reacted with 4-pyrrolidin-1-yl-piperidine to give the title compound as colorless solid. MS: 432.3 (MH+).

Example 28

[2,4-Dimethyl-6-(3-trifluoromethoxy-phenyl)-pyridin-3-yl]-(4-pyrrolidin-1-yl-piperidin-1-yl)-methanone

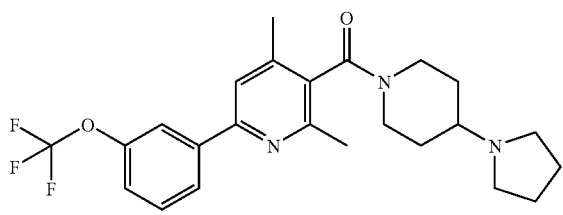

In analogy to the procedures described for example 1, for intermediate 5B and for intermediate 1, the title compound has been prepared by the following reaction sequence: i) 6-chloro-2,4-dimethyl-nicotinic acid ethyl ester [Zhou, Y.; Bridger, G. J.; Skerlj, R. T.; Bogucki, D.; Yang, W.; Bourque, E.; Langille, J.; Li, T.-S.; Metz, M. U.S. Pat. Appl. Publ. (2005), US 2005277668 A1] was reacted with 3-trifluoromethoxy-phenyl boronic acid to give 2,4-dimethyl-6-(3-trifluoromethoxy-phenyl)-nicotinic acid ethyl ester; ii) 2,4-dimethyl-6-(3-trifluoromethoxy-phenyl)-nicotinic acid ethyl ester has been saponified to give 2,4-dimethyl-6-(3-trifluoromethoxy-phenyl)-nicotinic acid; iii) 2,4-dimethyl-6-(3-trifluoromethoxy-phenyl)-nicotinic acid was converted into its acid chloride and reacted with 4-pyrrolidin-1-yl-piperidine to give the title compound as light yellow oil. MS: 448.2 (MH+).

Example 29

[2,4-Dimethyl-6-(3-trifluoromethoxy-phenyl)-pyridin-3-yl]-[4-((S)-2-hydroxymethyl-pyrrolidin-1-yl)-piperidin-1-yl]-methanone

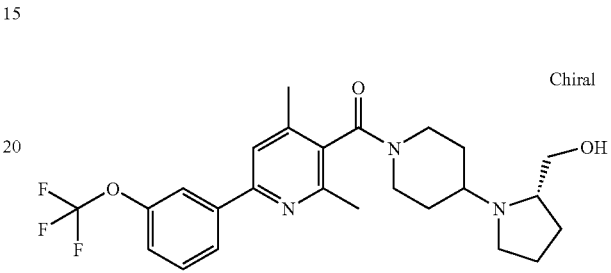

In analogy to the procedures described for intermediate 1 and for intermediate 4B,2,4-dimethyl-6-(3-trifluoromethoxy-phenyl)-nicotinic acid (example 28) was converted into its acid chloride and reacted with benzoic acid (S)-1-piperidin-4-yl-pyrrolidin-2-ylmethyl ester (intermediate 3) to give benzoic acid (S)-1-{1-[2,4-dimethyl-6-(3-trifluoromethoxy-phenyl)-pyridine-3-carbonyl]-piperidin-4-yl}-pyrrolidin-2-ylmethyl ester, which was subsequently saponified to give the title compound as colorless amorphous solid. MS: 478.2 (MH+).

Example 30

[2,4-Dimethyl-6-(3-trifluoromethyl-phenyl)-pyridin-3-yl]-[4-((S)-2-hydroxymethyl-pyrrolidin-1-yl)-piperidin-1-yl]-methanone

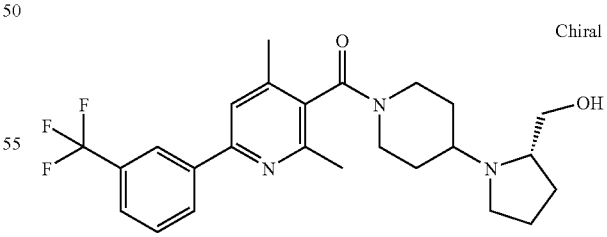

In analogy to the procedures described for intermediate 1 and for intermediate 4B,2,4-dimethyl-6-(3-trifluoromethyl-phenyl)-nicotinic acid (example 27) was converted into its acid chloride and reacted with benzoic acid (S)-1-piperidin-4-yl-pyrrolidin-2-ylmethyl ester (intermediate 3) to give benzoic acid (S)-1-{1-[2,4-dimethyl-6-(3-trifluoromethyl-phenyl)-pyridine-3-carbonyl]-piperidin-4-yl}-pyrrolidin-2-

Example 31

[4-Cyclopropyl-6-methyl-2-(3-trifluoromethyl-phenyl)-pyrimidin-5-yl]-(4-morpholin-4-yl-piperidin-1-yl)-methanone

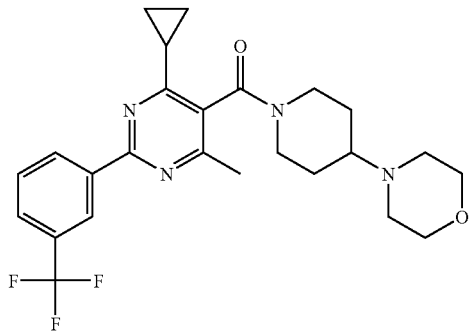

In analogy to the procedure described for intermediate 2,4-cyclopropyl-6-methyl-2-(3-trifluoromethyl-phenyl)-pyrimidine-5-carboxylic acid (intermediate 7) was reacted with HATU, triethylamine and 4-piperidin-4-yl-morpholine in DMF. Subsequent purification by preparative HPLC afforded the title compound as a gum. MS: 475.3 (MH$^+$).

Example 32

[1,4']Bipiperidinyl-1'-yl-[4-cyclopropyl-6-methyl-2-(3-trifluoromethyl-phenyl)-pyrimidin-5-yl]-methanone

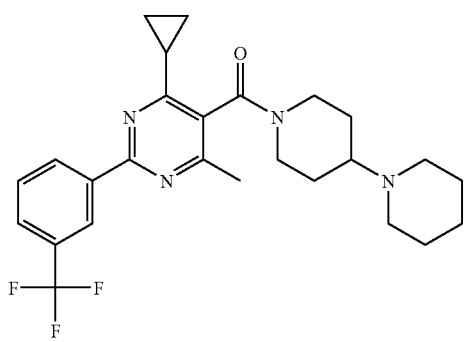

In analogy to the procedure described for intermediate 2,4-cyclopropyl-6-methyl-2-(3-trifluoromethyl-phenyl)-pyrimidine-5-carboxylic acid (intermediate 7) was reacted with HATU, triethylamine and [1,4']bipiperidinyl in DMF. Subsequent purification by preparative HPLC afforded the title compound as a gum. MS: 473.3 (MH$^+$).

Example 33

[4-Cyclopropyl-6-methyl-2-(3-trifluoromethyl-phenyl)-pyrimidin-5-yl]-(4-hydroxy-[1,4']bipiperidinyl-1'-yl)-methanone

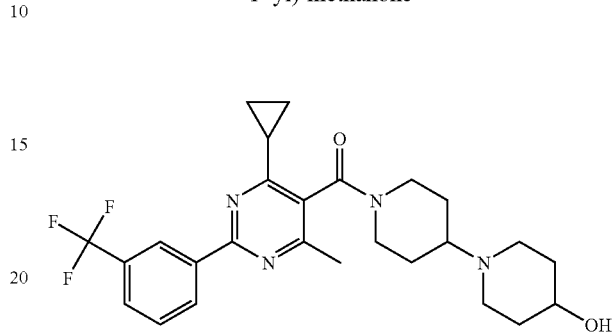

In analogy to the procedure described for intermediate 2,4-cyclopropyl-6-methyl-2-(3-trifluoromethyl-phenyl)-pyrimidine-5-carboxylic acid (intermediate 7) was reacted with HATU, triethylamine and [1,4']bipiperidinyl-4-ol in DMF. Subsequent purification by preparative HPLC afforded the title compound as a gum. MS: 489.3 (MH$^+$).

Example 34

(rac)-[4-Cyclopropyl-6-methyl-2-(3-trifluoromethyl-phenyl)-pyrimidin-5-yl]-(3-hydroxy-[1,4']bipiperidinyl-1'-yl)-methanone

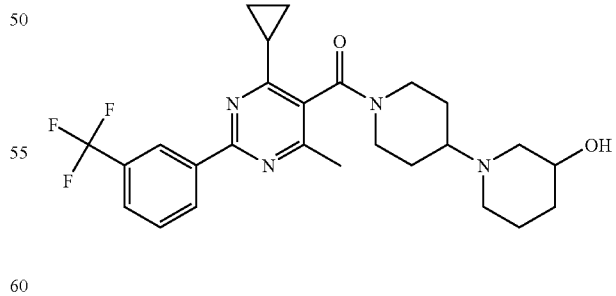

In analogy to the procedure described for intermediate 2,4-cyclopropyl-6-methyl-2-(3-trifluoromethyl-phenyl)-pyrimidine-5-carboxylic acid (intermediate 7) was reacted with HATU, triethylamine and (rac)-[1,4']bipiperidinyl-3-ol in DMF. Subsequent purification by preparative HPLC afforded the title compound as a gum. MS: 489.3 (MH⁺).

Example 35

(rac)-[4-Cyclopropyl-6-methyl-2-(3-trifluoromethyl-phenyl)-pyrimidin-5-yl]-(3-diethylamino-pyrrolidin-1-yl)-methanone

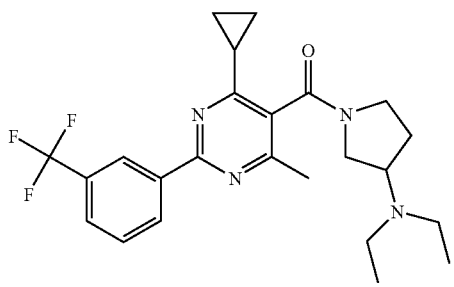

In analogy to the procedure described for intermediate 2,4-cyclopropyl-6-methyl-2-(3-trifluoromethyl-phenyl)-pyrimidine-5-carboxylic acid (intermediate 7) was reacted with HATU, triethylamine and (rac)-diethyl-pyrrolidin-3-yl-amine in DMF. Subsequent purification by preparative HPLC afforded the title compound as a gum. MS: 447.3 (MH⁺).

Example 36

[4-Cyclopropyl-6-methyl-2-(3-trifluoromethoxy-phenyl)-pyrimidin-5-yl]-(4-pyrrolidin-1-yl-piperidin-1-yl)-methanone

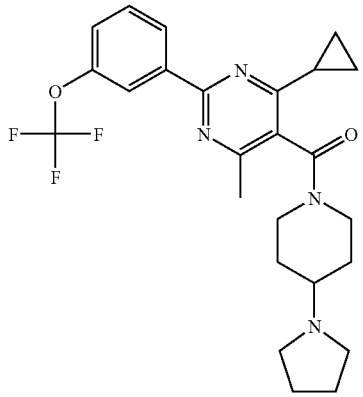

In analogy to the procedure described for intermediate 2,4-cyclopropyl-6-methyl-2-(3-trifluoromethoxy-phenyl)-pyrimidine-5-carboxylic acid [prepared in analogy to the preparation of 4-cyclopropyl-6-methyl-2-(3-trifluoromethyl-phenyl)-pyrimidine-5-carboxylic acid (intermediate 7), by using 3-trifluoromethoxy-benzamidine hydrochloride instead of 3-trifluoromethyl-benzamidine hydrochloride in the reaction step analogous to the preparation of intermediate 7A] was reacted with HATU, triethylamine and 4-pyrrolidin-1-yl-piperidine in DMF. Subsequent purification by preparative HPLC afforded the title compound as a gum. MS: 475.3 (MH⁺).

Example 37

[4-Cyclopropyl-6-methyl-2-(3-trifluoromethoxy-phenyl)-pyrimidin-5-yl]-[4-((S)-2-hydroxymethyl-pyrrolidin-1-yl)-piperidin-1-yl]-methanone

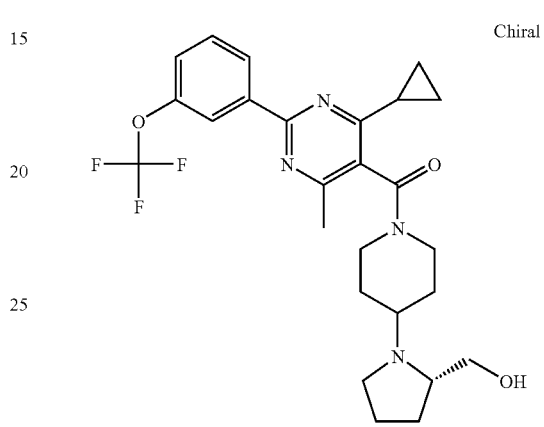

In analogy to the procedure described for intermediate 2,4-cyclopropyl-6-methyl-2-(3-trifluoromethoxy-phenyl)-pyrimidine-5-carboxylic acid (example 36) was reacted with HATU, triethylamine and ((S)-1-piperidin-4-yl-pyrrolidin-2-yl)-methanol di-hydrochloride (intermediate 9) in DMF. Subsequent purification by preparative HPLC afforded the title compound as a gum. MS: 505.3 (MH⁺).

Example 38

N-((3R,5S)-1-{1-[4-Cyclopropyl-6-methyl-2-(3-trifluoromethoxy-phenyl)-pyrimidine-5-carbonyl]-piperidin-4-yl}-5-hydroxymethyl-pyrrolidin-3-yl)-acetamide

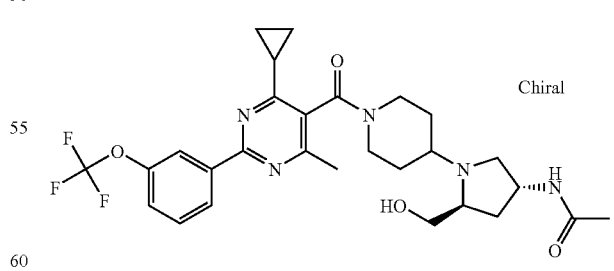

In analogy to the procedure described for intermediate 2,4-cyclopropyl-6-methyl-2-(3-trifluoromethoxy-phenyl)-pyrimidine-5-carboxylic acid (example 36) was reacted with HATU, triethylamine and N-((3R,5S)-5-hydroxymethyl-1-piperidin-4-yl-pyrrolidin-3-yl)-acetamide dihydrochloride (intermediate 8) in DMF. Subsequent purification by preparative HPLC afforded the title compound as a gum. MS: 562.3 (MH⁺).

Example 39

(3,5-Difluoro-3'-trifluoromethyl-biphenyl-4-yl)-(4-pyrrolidin-1-yl-piperidin-1-yl)-methanone

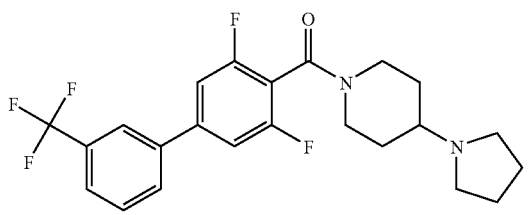

In analogy to the procedures described for intermediate 1 and for example 1, 4-bromo-2,6-difluoro-benzoyl chloride was reacted with 4-pyrrolidin-1-yl-piperidine and Et₃N in CH₂Cl₂ to give (4-bromo-2,6-difluoro-phenyl)-(4-pyrrolidin-1-yl-piperidin-1-yl)-methanone, which was then reacted with 3-trifluoromethyl-phenyl boronic acid to give the title compound as colorless oil. MS: 439.2 (MH⁺).

Example 40

(3,5-Difluoro-3'-trifluoromethoxy-biphenyl-4-yl)-(4-pyrrolidin-1-yl-piperidin-1-yl)-methanone

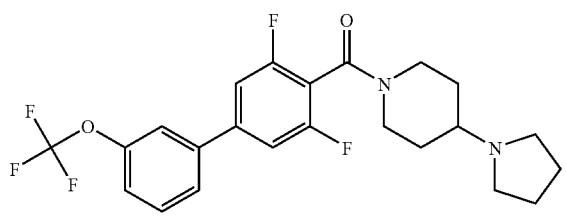

In analogy to the procedure described for example 1, (4-bromo-2,6-difluoro-phenyl)-(4-pyrrolidin-1-yl-piperidin-1-yl)-methanone (example 39) was reacted with 3-trifluoromethoxy-phenyl boronic acid to give the title compound as colorless oil. MS: 455.5 (MH⁺).

Example 41

(3,5-Difluoro-4'-trifluoromethoxy-biphenyl-4-yl)-(4-pyrrolidin-1-yl-piperidin-1-yl)-methanone

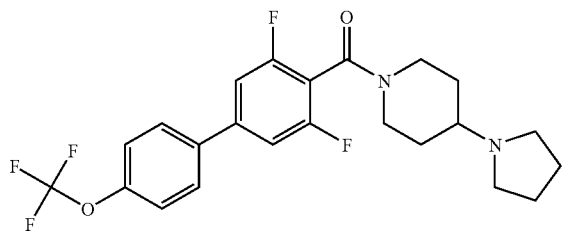

In analogy to the procedure described for example 1, (4-bromo-2,6-difluoro-phenyl)-(4-pyrrolidin-1-yl-piperidin-1-yl)-methanone (example 39) was reacted with 4-trifluoromethoxy-phenyl boronic acid to give the title compound as light yellow amorphous solid. MS: 455.5 (MH⁺).

Example 42

(4,6-Dimethyl-5'-trifluoromethyl-[2,3']bipyridinyl-5-yl)-(4-pyrrolidin-1-yl-piperidin-1-yl)-methanone

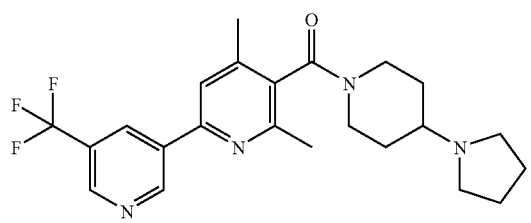

In analogy to the procedures described for example 1, for intermediate 5B and for intermediate 1, the title compound has been prepared by the following reaction sequence: i) 6-chloro-2,4-dimethyl-nicotinic acid ethyl ester [Zhou, Y.; Bridger, G. J.; Skerlj, R. T.; Bogucki, D.; Yang, W.; Bourque, E.; Langille, J.; Li, T.-S.; Metz, M. U.S. Pat. Appl. Publ. (2005), US 2005277668 A1] was reacted with 3-(4,4,5,5-tetramethyl-[1,3,2]dioxaborolan-2-yl)-5-trifluoromethyl-pyridine (intermediate 6) to give 4,6-dimethyl-5'-trifluoromethyl-[2,3']bipyridinyl-5-carboxylic acid ethyl ester; ii) 4,6-dimethyl-5'-trifluoromethyl-[2,3']bipyridinyl-5-carboxylic acid ethyl ester has been saponified to give 4,6-dimethyl-5'-trifluoromethyl-[2,3']bipyridinyl-5-carboxylic acid; iii) 4,6-dimethyl-5'-trifluoromethyl-[2,3']bipyridinyl-5-carboxylic acid was converted into its acid chloride and reacted with 4-pyrrolidin-1-yl-piperidine to give the title compound as colorless amorphous solid. MS: 433.3 (MH⁺).

Example 43

(4,6-Dimethyl-5'-trifluoromethyl-[2,3']bipyridinyl-5-yl)-[4-((S)-2-hydroxymethyl-pyrrolidin-1-yl)-piperidin-1-yl]-methanone

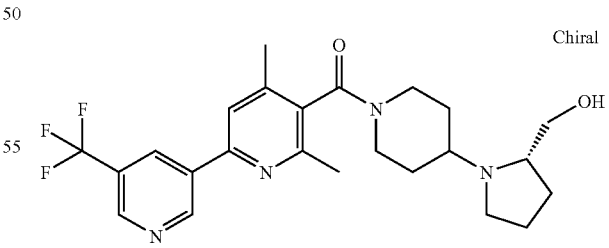

In analogy to the procedures described for intermediate 1 and for intermediate 4B, 4,6-dimethyl-5'-trifluoromethyl-[2,3']bipyridinyl-5-carboxylic acid (example 42) was converted into its acid chloride and reacted with benzoic acid (S)-1-piperidin-4-yl-pyrrolidin-2-ylmethyl ester (intermediate 3) to give benzoic acid (S)-1-[1-(4,6-dimethyl-5'-trifluoromethyl-[2,3']bipyridinyl-5-carbonyl)-piperidin-4-yl]-pyrrolidin-2-ylmethyl ester, which was subsequently saponified to give the title compound as colorless amorphous solid. MS: 463.2 (MH+).

Example 44

(3-Methoxy-5-methyl-3'-trifluoromethyl-biphenyl-4-yl)-(4-pyrrolidin-1-yl-piperidin-1-yl)-methanone

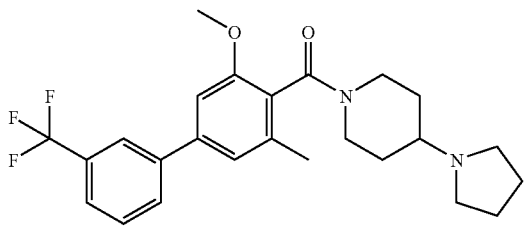

In analogy to the procedure described for intermediate 1,3-methoxy-5-methyl-3'-trifluoromethyl-biphenyl-4-carboxylic acid (intermediate 10) was converted into its acid chloride and reacted with 4-pyrrolidin-1-yl-piperidine to give the title compound as colorless amorphous solid. MS: 447.1 (MH+).

Example 45

(3-Hydroxy-5-methyl-3'-trifluoromethyl-biphenyl-4-yl)-(4-pyrrolidin-1-yl-piperidin-1-yl)-methanone

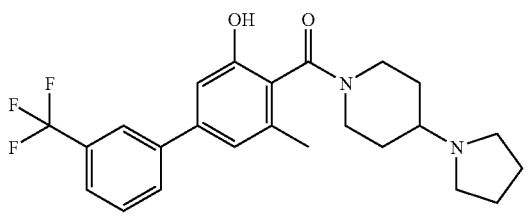

To a solution of 0.51 g (1.1 mmol) of (3-methoxy-5-methyl-3'-trifluoromethyl-biphenyl-4-yl)-(4-pyrrolidin-1-yl-piperidin-1-yl)-methanone (example 44) in 15 ml of $CH_2Cl_2$ was added at 0° C. 0.39 ml=0.57 g (2.3 mmol) of a boron tribromide solution (1.0 molar in $CH_2Cl_2$) drop by drop and the reaction mixture was the warmed up to RT. After 4 hours, it was poured into crashed ice, neutralized with sodium hydrogen carbonate solution and extracted twice with $CH_2Cl_2$; the organic phases were washed with water, dried over magnesium sulfate, filtered and evaporated. The residue was purified by flash column chromatography ($CH_2Cl_2$/MeOH 1:0 to 4:1) to give 0.18 g (36%) of the title compound as colorless amorphous solid. MS: 433.2 (MH+).

Example 46

(3-Chloro-3'-trifluoromethyl-biphenyl-4-yl)-(4-pyrrolidin-1-yl-piperidin-1-yl)-methanone

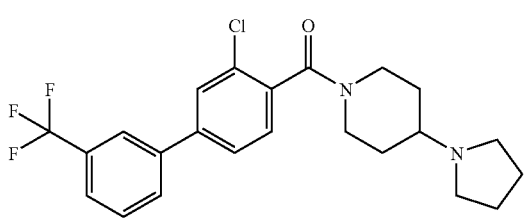

In analogy to the procedure described for example 1, (4-bromo-2-chloro-phenyl)-(4-pyrrolidin-1-yl-piperidin-1-yl)-methanone (prepared from 4-bromo-2-chloro-benzoic acid and 4-pyrrolidin-1-yl-piperidine in analogy to the procedure described for the preparation of intermediate 2), was reacted with 3-trifluoromethyl-phenyl boronic acid, potassium phosphate solution and tetrakis-(triphenylphosphine)-palladium in DMF while keeping the temperature at RT instead of 80° C. to give the title compound as light brown oil. MS: 437.2 (MH+, 1Cl).

Example 47

(5-Methyl-3-pyrimidin-5-yl-3'-trifluoromethyl-biphenyl-4-yl)-(4-pyrrolidin-1-yl-piperidin-1-yl)-methanone

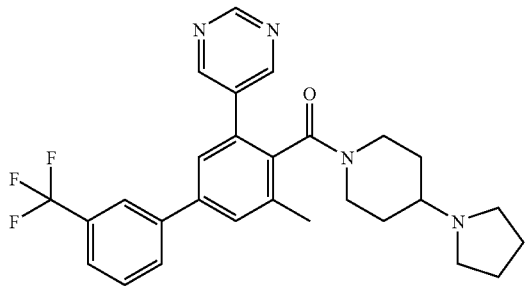

0.05 g (0.1 mmol) of 5-methyl-3-pyrimidin-5-yl-3'-trifluoromethyl-biphenyl-4-carboxylic acid (intermediate 11) in 1.0 ml of oxalyl chloride (11.7 mmol) was treated at RT while stirring with one drop of DMF; after 30 min, the excess of oxalyl chloride was removed by evaporation in a high vacuum at RT. The residue was dissolved in 2.0 ml of $CH_2Cl_2$ and cooled down to 0° C.; then, 0.08 ml=0.056 g (0.6 mmol) of $Et_3N$ was added while stirring, followed by 0.022 g (0.1 mmol) of 4-pyrrolidin-1-yl-piperidine. The reaction mixture was subsequently warmed up to RT. After two hours, it was poured into crashed ice and extracted twice with $CH_2Cl_2$; the organic phases were washed with water, dried over magnesium sulfate, filtered and evaporated. The residue was purified by flash column chromatography ($CH_2Cl_2$/MeOH 1:0 to 4:1) to give 0.049 g (71%) of the title compound as yellow solid. MS: 495.3 (MH+).

Example 48

(5-Methyl-3-pyridin-3-yl-3' trifluoromethyl-biphenyl-4-yl)-(4-pyrrolidin-1-yl-piperidin-1-yl)-methanone

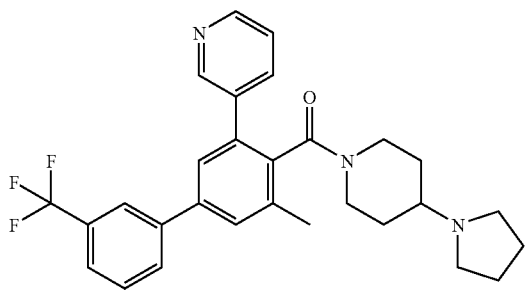

In analogy to the procedures described in example 1, intermediate 11 E and in example 47, the title compound has been prepared by the following reaction sequence: i) 5-methyl-3-trifluoromethanesulfonyloxy-3'-trifluoromethyl-biphenyl-4-carboxylic acid methyl ester (intermediate 11 C) was reacted with pyridine-3-yl-boronic acid in DMF at 80° C. in the presence of potassium phosphate solution and tetrakis-(triphenylphosphine)-palladium to give 5-methyl-3-pyridin-3-yl-3'-trifluoromethyl-biphenyl-4-carboxylic acid methyl ester; ii) saponification of 5-methyl-3-pyridin-3-yl-3'-trifluoromethyl-biphenyl-4-carboxylic acid methyl ester gave 5-methyl-3-pyridin-3-yl-3'-trifluoromethyl-biphenyl-4-carboxylic acid; iii) transformation of 5-methyl-3-pyridin-3-yl-3'-trifluoromethyl-biphenyl-4-carboxylic acid into its acid chloride and reaction with 4-pyrrolidin-1-yl-piperidine gave the title compound as off-white amorphous solid. MS: 494.3 (MH$^+$).

Example 49

(3-Methoxy-3'-trifluoromethyl-biphenyl-4-yl)-(4-pyrrolidin-1-yl-piperidin-1-yl)-methanone

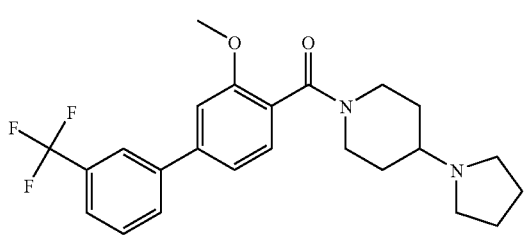

In analogy to the procedure described in example 1, (4-bromo-2-methoxy-phenyl)-(4-pyrrolidin-1-yl-piperidin-1-yl)-methanone (prepared from 4-bromo-2-methoxybenzoic acid and 4-pyrrolidin-1-yl-piperidine in analogy to the procedure described for the preparation of intermediate 2), was reacted with 3-trifluoromethyl-phenyl boronic acid, potassium phosphate solution and tetrakis-(triphenylphosphine)-palladium in DMF at 80° C. to give the title compound as colorless oil. MS: 433.2 (MH$^+$).

Example 50

[2-Methoxy-4-methyl-6-(3-trifluoromethyl-phenyl)-pyridin-3-yl]-(4-pyrrolidin-1-yl-piperidin-1-yl)-methanone

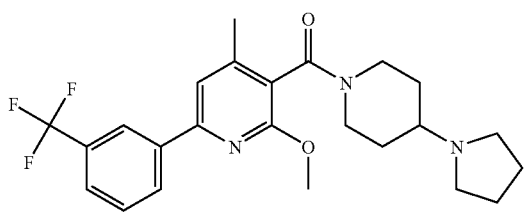

In analogy to the procedure described for intermediate 1, 2-methoxy-4-methyl-6-(3-trifluoromethyl-phenyl)-nicotinic acid (intermediate 12) was converted into its acid chloride and reacted with 4-pyrrolidin-1-yl-piperidine to give the title compound as yellow amorphous solid. MS: 448.1 (MH$^+$).

Example 51

[2-Hydroxy-4-methyl-6-(3-trifluoromethyl-phenyl)-pyridin-3-yl]-(4-pyrrolidin-1-yl-piperidin-1-yl)-methanone; 4-Methyl-3-(4-pyrrolidin-1-yl-piperidine-1-carbonyl)-6-(3-trifluoromethyl-phenyl)-1H-pyridin-2-one (tautomers)

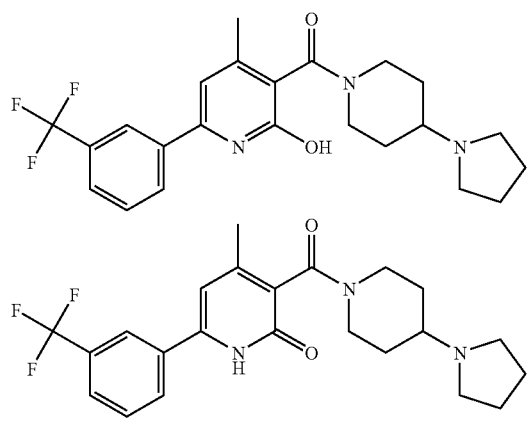

A solution of 5.25 g (11.7 mmol) of [2-methoxy-4-methyl-6-(3-trifluoromethyl-phenyl)-pyridin-3-yl]-(4-pyrrolidin-1-yl-piperidin-1-yl)-methanone (example 50) in 180 ml of CH$_2$Cl$_2$ was cooled down to 0° C. and 23.5 ml (23.5 mmol) of a boron tribromide solution (1 molar in CH$_2$Cl$_2$) was added drop by drop. After stirring for 1 hour at RT, the reaction mixture was added drop by drop to a cold solution of NaHCO$_3$ (saturated in water) and it was then extracted twice with MeCl$_2$; the organic phases were washed with water, dried over magnesium sulfate, filtered and evaporated. The residue was purified by flash column chromatography (CH$_2$Cl$_2$/MeOH 98:2 to 4:1) to give 4.96 g (98%) of the title compound as light yellow solid. MS: 434.3 (MH$^+$).

Example 52

[2-(2-Benzyloxy-ethoxy)-4-methyl-6-(3-trifluoromethyl-phenyl)-pyridin-3-yl]-(4-pyrrolidin-1-yl-piperidin-1-yl)-methanone

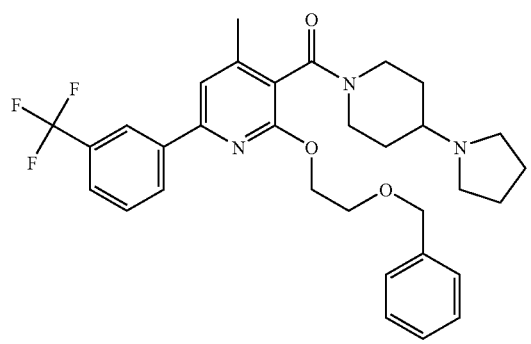

In analogy to the procedure described for intermediate 1,2-(2-benzyloxy-ethoxy)-4-methyl-6-(3-trifluoromethyl-phenyl)-nicotinic acid (intermediate 13) was converted into its acid chloride and reacted with 4-pyrrolidin-1-yl-piperidine to give the title compound as light yellow oil. MS: 468.4 (MH$^+$).

Example 53

[2-(2-Hydroxy-ethoxy)-4-methyl-6-(3-trifluoromethyl-phenyl)-pyridin-3-yl]-(4-pyrrolidin-1-yl-piperidin-1-yl)-methanone

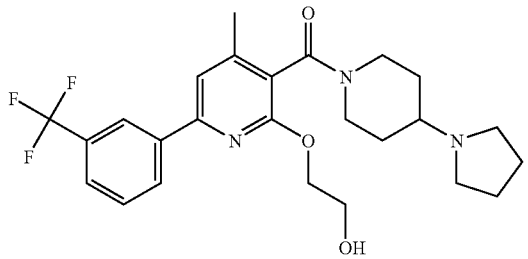

A solution of 0.22 g (0.4 mmol) of [2-(2-benzyloxy-ethoxy)-4-methyl-6-(3-trifluoromethyl-phenyl)-pyridin-3-yl]-(4-pyrrolidin-1-yl-piperidin-1-yl)-methanone (example 52) in 10 ml of MeOH was treated with 0.04 g (0.04 mmol) of Pd—C (10%) and 0.5 ml of HCl/MeOH (1 molar). The reaction mixture was hydrogenated at RT and ambient pressure until the absorption of H$_2$ stopped (1 hour). After filtration with the aid of Dicalite, the filtrate was poured into crashed ice, the pH was adjusted to 8-9 with the help of sodium carbonate solution and the reaction mixture was extracted twice with CH$_2$Cl$_2$; the organic phases were washed with water, dried over magnesium sulfate, filtered and evaporated. The residue was purified by flash column chromatography [CH$_2$Cl$_2$ (sat. with NH$_3$)/MeOH 98:2 to 4:1] to give 0.16 g (86%) of the title compound as colorless oil. MS: 478.2 (MH$^+$).

Example 54

(3-Methanesulfonyl-3'-trifluoromethyl-biphenyl-4-yl)-(4-pyrrolidin-1-yl-piperidin-1-yl)-methanone

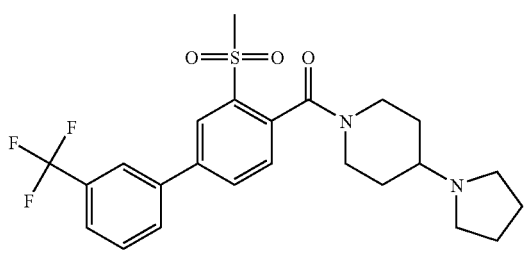

In analogy to the procedure described in example 1, (4-bromo-2-methanesulfonyl-phenyl)-(4-pyrrolidin-1-yl-piperidin-1-yl)-methanone (prepared from 4-bromo-2-methanesulfonyl-benzoic acid and 4-pyrrolidin-1-yl-piperidine in analogy to the procedure described for the preparation of intermediate 2) was reacted with 3-trifluoromethyl-phenyl boronic acid, potassium phosphate solution and tetrakis-(triphenylphosphine)-palladium in DMF at 80° C. to give the title compound as light yellow oil. MS: 481.2 (MH$^+$).

Example A

Film coated tablets containing the following ingredients can be manufactured in a conventional manner:

| Ingredients | Per tablet | |
| --- | --- | --- |
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
| --- | --- |
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
| --- | --- |
| Compound of formula (I) | 3.0 mg |
| Polyethylene Glycol 400 | 150.0 mg |
| Acetic Acid | q.s. ad pH 5.0 |
| Water for injection solutions | Ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| Compound of formula (I) | 50.0 mg |
| --- | --- |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavouring additives and filled into sachets.

The invention claimed is:

1. A compound of formula (I)

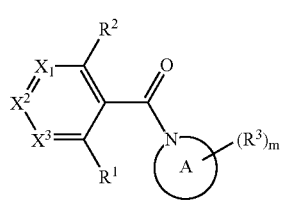

wherein $R^1$ is halogen, $C_{1-6}$ alkyl, $C_{1-6}$ alkoxy, halo $C_{1-6}$ alkyl, heteroalkyl, $C_{1-6}$ alkylsulfanyl, $C_{1-6}$ alkylsulfinyl, $C_{1-6}$ alkylsulfonyl, $C_{3-7}$ cycloalkyl or $C_{3-7}$ cycloalkyl $C_{1-6}$ alkyl;

$R^2$ is hydrogen, $C_{1-6}$ alkyl, halo $C_{1-6}$ alkyl, trimethylsilanyl $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, trimethylsilanyl $C_{2-6}$ alkynyl, hydroxy, $C_{1-6}$ alkoxy, halo $C_{1-6}$ alkoxy, heteroalkoxy, optionally substituted $C_{3-7}$ cycloalkyl, optionally substituted $C_{3-7}$ cycloalkyl $C_{1-6}$ alkyl, halogen, cyano, optionally substituted phenyl, optionally substituted heteroaryl, optionally substituted heterocyclyl or optionally substituted phenylmethoxy-$C_{1-6}$ alkoxy, provided that the optionally substituted phenyl does not have nitro as a substituent;

$R^3$ is, when attached to a ring carbon atom, independently hydrogen, $C_{1-6}$ alkyl, halo $C_{1-6}$ alkyl, heteroalkyl, $C_{2-6}$ alkenyl, $C_{2-6}$ alkynyl, hydroxy $C_{3-6}$ alkenyl, hydroxy $C_{3-6}$ alkynyl, $C_{1-6}$ alkoxy $C_{3-6}$ alkenyl, $C_{1-6}$ alkoxy $C_{3-6}$ alkynyl, hydroxy, $C_{1-6}$ alkoxy, halo $C_{1-6}$ alkoxy, heteroalkoxy, halogen, cyano, optionally substituted phenyl, optionally substituted $C_{3-7}$ cycloalkyl, optionally substituted $C_{3-7}$ cycloalkyl $C_{1-6}$ alkyl, optionally substituted heteroaryl, optionally substituted heterocyclyl, optionally substituted phenyl-$C_{1-6}$ alkyl, optionally substituted heteroaryl-$C_{1-6}$ alkyl, optionally substituted heterocyclyl-$C_{1-6}$ alkyl, nitro, carboxy, formyl, acyl, $C_{1-6}$ alkoxycarbonyl, carbamoyl, mono- or di-$C_{1-6}$ alkyl substituted aminocarbonyl, $C_{1-6}$ alkylthio, $C_{1-6}$ alkylsulfinyl or $C_{1-6}$ alkylsulfonyl or amino optionally substituted by one or two substituents independently selected from the group consisting of $C_{1-6}$ alkyl, heteroalkyl, optionally substituted $C_{3-7}$ cycloalkyl and optionally substituted heterocyclyl; or m is 0, 1, 2, 3 or 4;

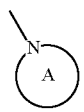

is piperidin-1-yl;

$X^2$ is C—$R^4$ wherein $R^4$ is phenyl or pyridyl, said phenyl and pyridyl being substituted by halo $C_{1-6}$ alkyl or halo $C_{1-6}$ alkyoxy;

and both $X^1$ and $X^3$ are N or C—$R^5$ wherein $R^5$ is hydrogen;

or pharmaceutically acceptable salts thereof.

2. The compound of claim 1, wherein m is 1.

3. The compound of claim 1 wherein $R^3$ is optionally substituted heterocyclyl or heteroalkyl.

4. The compound of claim 1 wherein $R^3$ is hydroxy $C_{1-6}$ alkyl, optionally substituted pyrrolidin-1-yl or optionally substituted piperidin-1-yl.

5. The compound of claim 1 wherein $R^3$ is piperidin-1-yl or pyrrolidin-1-yl, said piperidin-1-yl and pyrrolidin-1-yl being optionally substituted by hydroxyl $C_{1-6}$ alkyl or hydroxy.

6. The compound of claim 1 wherein $R^3$ is pyrrolidin-1-yl, 2-hydroxymethyl-pyrrolidin-1-yl or 4-hydroxy-piperidin-1-yl.

7. The compound of claim 1 wherein

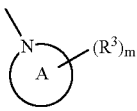

is 4-pyrrolidin-1-yl-piperidin-1-yl, 4-(2-hydroxymethyl-pyrrolidin-1-yl)-piperidin-1-yl or 4-hydroxy-[1,4']bipiperidinyl-1'-yl.

8. The compound of claim 1 wherein $R^1$ is halogen or $C_{1-6}$ alkyl and $R^2$ is hydrogen, hydroxy, halogen, $C_{1-6}$ alkyl, optionally substituted heteroaryl, heteroalkoxy or cyclopropyl.

9. The compound of claim 8 wherein $R^1$ is fluorine or methyl and $R^2$ is hydrogen, hydroxy, fluorine, methyl, pyrimidinyl, pyridinyl, hydroxyethoxy or cyclopropyl.

10. The compound of claim 8 wherein $R^1$ is $C_{1-6}$ alkyl and $R^2$ is hydrogen, $C_{1-6}$ alkyl or cyclopropyl.

11. The compound of claim 10, wherein $R^1$ is methyl and $R^2$ is methyl or cyclopropyl.

12. The compound of claim 1, selected from the group consisting of
- (3,5-Dimethyl-3'-trifluoromethoxy-biphenyl-4-yl)-(4-pyrrolidin-1-yl-piperidin-1-yl)-methanone,
- (3,5-Dimethyl-3'-trifluoromethyl-biphenyl-4-yl)-(4-pyrrolidin-1-yl-piperidin-1-yl)-methanone,
- (3,5-Dimethyl-3'-trifluoromethyl-biphenyl-4-yl)-[4-((S)-2-hydroxymethyl-pyrrolidin-1-yl)-piperidin-1-yl]-methanone,
- [2,6-Dimethyl-4-(5-trifluoromethyl-pyridin-3-yl)-phenyl]-[4-((S)-2-hydroxymethyl-pyrrolidin-1-yl)-piperidin-1-yl]-methanone,
- [4-Cyclopropyl-6-methyl-2-(3-trifluoromethyl-phenyl)-pyrimidin-5-yl]-(4-pyrrolidin-1-yl-piperidin-1-yl)-methanone,
- (3,5-Dimethyl-3'-trifluoromethyl-biphenyl-4-yl)-(4-hydroxy-[1,4']bipiperidinyl-1'-yl)-methanone,
- [2,4-Dimethyl-6-(3-trifluoromethyl-phenyl)-pyridin-3-yl]-(4-pyrrolidin-1-yl-piperidin-1-yl)-methanone,
- (3,5-Difluoro-3'-trifluoromethyl-biphenyl-4-yl)-(4-pyrrolidin-1-yl-piperidin-1-yl)-methanone,
- (5-Methyl-3-pyrimidin-5-yl-3'-trifluoromethyl-biphenyl-4-yl)-(4-pyrrolidin-1-yl-piperidin-1-yl)-methanone,
- (5-Methyl-3-pyridin-3-yl-3'-trifluoromethyl-biphenyl-4-yl)-(4-pyrrolidin-1-yl-piperidin-1-yl)-methanone,
- [2-Hydroxy-4-methyl-6-(3-trifluoromethyl-phenyl)-pyridin-3-yl]-(4-pyrrolidin-1-yl-piperidin-1-yl)-methanone; 4-Methyl-3-(4-pyrrolidin-1-yl-piperidine-1-carbonyl)-6-(3-trifluoromethyl-phenyl)-1H-pyridin-2-one, and
- [2-(2-Hydroxy-ethoxy)-4-methyl-6-(3-trifluoromethyl-phenyl)-pyridin-3-yl]-(4-pyrrolidin-1-yl-piperidin-1-yl)-methanone.

13. A pharmaceutical composition comprising a therapeutically effective amount of the compound of claim 1 and a pharmaceutically acceptable excipient.

* * * * *